US012102118B2

(12) United States Patent
Sur et al.

(10) Patent No.: US 12,102,118 B2
(45) Date of Patent: Oct. 1, 2024

(54) ELECTRONICALLY HEATED HEAT-NOT-BURN SMOKING ARTICLE

(71) Applicant: RAI STRATEGIC HOLDINGS, INC., Winston-Salem, NC (US)

(72) Inventors: Rajesh Sur, Winston-Salem, NC (US); Kathryn Lynn Wilberding, High Point, NC (US); Andries Sebastian, Clemmons, NC (US); Stephen Benson Sears, Siler City, NC (US); Timothy Frederick Thomas, High Point, NC (US); Sawyer Hubbard, Winston-Salem, NC (US); Billy Tyrone Conner, Clemmons, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 257 days.

(21) Appl. No.: 15/916,834

(22) Filed: Mar. 9, 2018

(65) Prior Publication Data

US 2019/0274354 A1    Sep. 12, 2019

(51) Int. Cl.
*A24D 1/20* (2020.01)
*A24F 40/20* (2020.01)
(Continued)

(52) U.S. Cl.
CPC ............... *A24D 1/20* (2020.01); *A24F 40/46* (2020.01); *A24F 40/50* (2020.01); *H05B 3/44* (2013.01);
(Continued)

(58) Field of Classification Search
CPC ............ A24F 47/008; H05B 3/44; H05B 3/46
(Continued)

(56) References Cited

U.S. PATENT DOCUMENTS

| 2,057,353 A | 10/1936 | Whittemore, Jr. |
| 2,104,266 A | 1/1938 | McCormick |

(Continued)

FOREIGN PATENT DOCUMENTS

| CN | 1541577 | 11/2004 |
| CN | 2719043 | 8/2005 |

(Continued)

OTHER PUBLICATIONS

International Search Report from corresponding International Appl. No. PCT/IB2019/051867, mailed Nov. 26, 2019.
(Continued)

*Primary Examiner* — Thien S Tran
(74) *Attorney, Agent, or Firm* — WOMBLE BOND DICKINSON (US) LLP

(57) ABSTRACT

Aerosol delivery devices are disclosed herein. In one aspect, an aerosol delivery device may comprise a control body, a heating member, a control component, a power source, and a removable aerosol source member that includes an inhalable substance medium, the aerosol source member being configured to be inserted into the control body and defining a heated end and a mouth end, the heated end configured, when inserted into the control body, to be positioned proximate the heating member. In some implementations, the heating member may comprise a base heating member and a substrate heating member, wherein the base heating member is located in the control body and the substrate heating member is located in the aerosol source member. In some implementations, the heating member may comprise a flexible heating member that surrounds a heating cylinder located within a portion of the engaging end of the control body.

3 Claims, 12 Drawing Sheets

(51) Int. Cl.
  *A24F 40/46* (2020.01)
  *A24F 40/50* (2020.01)
  *A24F 40/60* (2020.01)
  *H05B 3/44* (2006.01)
  *H05B 3/46* (2006.01)

(52) U.S. Cl.
  CPC .............. *H05B 3/46* (2013.01); *A24F 40/20* (2020.01); *A24F 40/60* (2020.01)

(58) Field of Classification Search
  USPC ........ 131/194, 273, 328, 329; 219/227, 260, 219/535
  See application file for complete search history.

(56) References Cited

U.S. PATENT DOCUMENTS

| | | | |
|---|---|---|---|
| 3,200,819 A | | 8/1965 | Gilbert |
| 4,922,901 A | | 5/1990 | Brooks et al. |
| 5,060,671 A | | 10/1991 | Counts et al. |
| 5,093,894 A | | 3/1992 | Deevi et al. |
| 5,261,424 A | | 11/1993 | Sprinkel, Jr. |
| 5,388,574 A | | 2/1995 | Ingebrethsen et al. |
| 5,479,948 A | | 1/1996 | Counts et al. |
| 5,530,225 A | | 6/1996 | Hajaligol |
| 5,591,368 A | | 1/1997 | Fleischhauer et al. |
| 5,687,746 A | | 11/1997 | Rose et al. |
| 5,726,421 A | | 3/1998 | Fleischhauer et al. |
| 5,865,185 A | | 2/1999 | Collins et al. |
| 5,894,841 A | | 4/1999 | Voges |
| 6,125,853 A | * | 10/2000 | Susa ........................ A61L 9/03 131/273 |
| 6,155,268 A | | 12/2000 | Takeuchi |
| 7,117,867 B2 | | 10/2006 | Cox et al. |
| 7,832,410 B2 | | 11/2010 | Hon |
| 8,314,591 B2 | | 11/2012 | Terry et al. |
| 8,365,742 B2 | | 2/2013 | Hon |
| 8,499,766 B1 | | 8/2013 | Newton |
| 8,973,587 B2 | | 3/2015 | Liu |
| 9,332,787 B2 | | 5/2016 | Liu |
| 2005/0016550 A1 | | 1/2005 | Katase |
| 2006/0196518 A1 | | 9/2006 | Hon |
| 2008/0092912 A1 | * | 4/2008 | Robinson ............... A24B 13/02 131/200 |
| 2009/0095311 A1 | | 4/2009 | Hon |
| 2009/0126745 A1 | | 5/2009 | Hon |
| 2009/0188490 A1 | | 7/2009 | Hon |
| 2009/0230117 A1 | * | 9/2009 | Fernando ................. H05B 3/20 219/490 |
| 2009/0272379 A1 | | 11/2009 | Thorens et al. |
| 2011/0094523 A1 | | 4/2011 | Thorens et al. |
| 2011/0126848 A1 | * | 6/2011 | Zuber ................... A24F 47/008 131/329 |
| 2011/0155718 A1 | | 6/2011 | Greim et al. |
| 2011/0168194 A1 | | 7/2011 | Hon |
| 2011/0265806 A1 | | 11/2011 | Alarcon et al. |
| 2011/0290248 A1 | | 12/2011 | Schennum |
| 2012/0111347 A1 | | 5/2012 | Hon |
| 2012/0260927 A1 | | 10/2012 | Liu |
| 2012/0279512 A1 | | 11/2012 | Hon |
| 2013/0037041 A1 | * | 2/2013 | Worm ................... A24F 47/008 131/329 |
| 2013/0056013 A1 | | 3/2013 | Terry et al. |
| 2013/0169230 A1 | | 7/2013 | Li et al. |
| 2013/0306084 A1 | | 11/2013 | Flick |
| 2014/0000638 A1 | | 1/2014 | Sebastian et al. |
| 2014/0060554 A1 | | 3/2014 | Collett et al. |
| 2014/0060555 A1 | | 3/2014 | Chang et al. |
| 2014/0096781 A1 | | 4/2014 | Sears et al. |
| 2014/0096782 A1 | | 4/2014 | Ampolini et al. |
| 2014/0209105 A1 | | 7/2014 | Sears et al. |
| 2014/0253144 A1 | | 9/2014 | Novak et al. |
| 2014/0261408 A1 | | 9/2014 | DePiano et al. |
| 2014/0261486 A1 | | 9/2014 | Potter et al. |
| 2014/0261487 A1 | | 9/2014 | Chapman et al. |
| 2014/0261495 A1 | | 9/2014 | Novak et al. |
| 2014/0270727 A1 | | 9/2014 | Ampolini et al. |
| 2014/0270729 A1 | | 9/2014 | DePiano et al. |
| 2014/0270730 A1 | | 9/2014 | DePiano et al. |
| 2014/0299137 A1 | * | 10/2014 | Kieckbusch .......... A24F 47/008 131/328 |
| 2014/0305449 A1 | * | 10/2014 | Plojoux ................. A24F 47/008 131/328 |
| 2014/0334802 A1 | * | 11/2014 | Dubief .................. A24F 40/485 392/390 |
| 2014/0366896 A1 | | 12/2014 | Li et al. |
| 2015/0059780 A1 | * | 3/2015 | Davis .................... A24F 47/008 131/328 |
| 2015/0209530 A1 | * | 7/2015 | White .................. A61M 11/042 424/729 |
| 2016/0255879 A1 | * | 9/2016 | Paprocki .............. H05B 1/0291 |
| 2016/0360786 A1 | * | 12/2016 | Bellinger ............. H05B 1/0227 |
| 2017/0360102 A1 | | 12/2017 | Li et al. |
| 2018/0310623 A1 | * | 11/2018 | Batista ................. A24F 40/465 |

FOREIGN PATENT DOCUMENTS

| | | |
|---|---|---|
| CN | 201379072 | 1/2010 |
| CN | 202907797 U | 5/2013 |
| EP | 0 295 122 | 12/1988 |
| EP | 0503767 A1 | 9/1992 |
| EP | 0 845 220 | 6/1998 |
| EP | 0703734 B1 | 6/2000 |
| EP | 1 618 803 | 1/2006 |
| EP | 2 368 449 A1 | 9/2011 |
| EP | 3 020 291 A1 | 8/2012 |
| GB | 2469850 | 11/2010 |
| GB | 2515502 A | 12/2014 |
| JP | H05-115272 A | 5/1993 |
| JP | H6-30753 A | 2/1994 |
| JP | H08-511176 A | 11/1996 |
| JP | 2010-047389 A | 3/2010 |
| JP | 2016-509481 A | 3/2016 |
| JP | 2016-534730 A | 11/2016 |
| JP | 2017-153496 A | 9/2017 |
| JP | 2017-184761 A | 10/2017 |
| JP | 2018-505696 A | 3/2018 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | 2010/047389 A1 | 4/2010 |
| WO | 2016/156609 A1 | 10/2016 |
| WO | 2016/159013 A1 | 10/2016 |
| WO | 2017/033007 A1 | 3/2017 |
| WO | 2017/068100 A1 | 4/2017 |
| WO | WO-2017068101 A1 * | 4/2017 ........... A24F 40/465 |
| WO | 2017/162691 A1 | 9/2017 |
| WO | 2017/194762 A1 | 11/2017 |
| WO | 2018/019578 A1 | 2/2018 |
| WO | 2018/037562 A1 | 3/2018 |
| WO | 2018/100497 A1 | 6/2018 |

OTHER PUBLICATIONS

Partial International Search Report from corresponding International Appl. No. PCT/IB2019/051867, mailed Jul. 8, 2019.

Extended European Search Report mailed Mar. 28, 2023 in the corresponding European Patent Application No. 22214487.5.

* cited by examiner

ELECTRONICALLY HEATED HEAT-NOT-BURN SMOKING ARTICLE

BACKGROUND

Field of the Disclosure

The present disclosure relates to aerosol delivery articles and uses thereof for yielding tobacco components or other materials in inhalable form. More particularly, the present disclosure relates to aerosol delivery devices and systems, such as smoking articles, that utilize electrically-generated heat to heat tobacco or a tobacco derived material, preferably without significant combustion, in order to provide an inhalable substance in the form of an aerosol for human consumption.

Description of Related Art

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and PCT Pat. App. Pub. No. WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™; IQOS™ by Philip Morris International; and GLO™ by British American Tobacco."

Articles that produce the taste and sensation of smoking by electrically heating tobacco or tobacco derived materials have suffered from inconsistent performance characteristics. Electrically heated smoking devices have further been limited in many instances by requiring large battery capabilities. Accordingly, it is desirable to provide a smoking article that can provide the sensations of cigarette, cigar, or pipe smoking, without substantial combustion, and that does so with increased performance characteristics.

BRIEF SUMMARY

In various implementations, the present disclosure provides an aerosol delivery device configured to yield an inhalable substance. In one implementation, the aerosol delivery device may comprise a substantially tubular control body having a closed distal end and an open engaging end, a heating member, a control component located within the control body and configured to control the heating member, a power source located within the control body and configured to provide power to the control component, and a substantially cylindrical removable aerosol source member that includes an inhalable substance medium, the aerosol source member being configured to be inserted into the engaging end of the control body and defining a heated end and a mouth end, the heated end configured, when inserted into the control body, to be positioned proximate the heating member, and the mouth end configured to extend beyond the engaging end of the control body. The heating member may be configured to provide heat to at least a portion of the aerosol source member so as to form an inhalable aerosol, the aerosol configured to be drawn through the aerosol source member in response to a draw applied to the mouth end of the inhalable substance medium, and the heating member may comprise a flexible heating member that surrounds a heating cylinder located within a portion of the engaging end of the control body.

In some implementations, at least a portion of the heating member may be in direct contact with the inhalable substance medium. In some implementations, the control component may be configured to provide an operating current that is at or between a range of approximately 2.5 Amps to approximately 10 Amps. In some implementations, the control component may be configured to provide up to approximately 96% efficiency of the power source. In some implementations, the control component may be configured to establish a time to reach temperature of less than approximately 10 seconds. In some implementations, the inhalable substance medium may include tobacco or a tobacco-derived material. In some implementations, at least a portion of the inhalable substance medium may comprise at least one of tobacco-containing beads, tobacco shreds, tobacco strips, pieces of a reconstituted tobacco material, and a tobacco cast sheet. In some implementations, at least a portion of the inhalable substance medium may comprise an extruded structure (with or without a central opening) that includes tobacco or a tobacco-derived material. In some implementations, the aerosol source member may include an overwrap comprising a paper material that surrounds the inhalable substance medium. In some implementations, the aerosol source member may include filter material located proximate the mouth end of the aerosol source member. In some implementations, the mouth end of the aerosol source member may be partially occluded. In some implementations, the control body may further include one or more ventilation openings configured to allow entry of ambient air into the control body.

Some implementations may further comprise a puff-activated switch that actuates current flow from the power source to the heating member. Some implementations may further comprise a manually operated pushbutton that actuates current flow from the power source to the heating member. In some implementations, the power source may comprise a battery. Some implementations may further comprise a current regulating component configured to regulate a previously initiated current flow from the power source to the heating member. In some implementations, the current regulating component may comprise a time-based component. In some implementations, the current regulating component may be configured to stop current to the electrical heating member once a defined temperature has been achieved. In some implementations, the current regulating component may be configured to cycle the current to the electrical heating member off and on once a defined temperature has been achieved so as to maintain the defined temperature for a defined period of time. In some implementations, the aerosol source member may define an outer surface, and fluid passage along the length of the aerosol source member may be substantially limited to passage within the aerosol source member.

In another implementation, the aerosol delivery device may comprise a substantially tubular control body having a closed distal end and an open engaging end, a heating member, a control component located within the control body and configured to control the heating member, a power source located within the control body and configured to provide power to the control component, and a substantially cylindrical removable aerosol source member that includes an inhalable substance medium, the aerosol source member being configured to be inserted into the engaging end of the control body and defining a heated end and a mouth end, the heated end configured, when inserted into the control body, to be positioned proximate the heating member, and the mouth end configured to extend beyond the engaging end of the control body. The heating member may be configured to provide heat to at least a portion of the aerosol source member so as to form an inhalable aerosol, the aerosol configured to be drawn through the aerosol source member in response to a draw applied to the mouth end of the inhalable substance medium, and the heating member may comprise a base heating member and a substrate heating member, wherein the base heating member is located in the control body and the substrate heating member is located in the aerosol source member, and wherein the base heating member is configured to transfer heat to the substrate heating member.

In some implementations, at least a portion of the heating member may be in direct contact with the inhalable substance medium. In some implementations, the control component may be configured to provide an operating current that is at or between a range of approximately 2.5 Amps to approximately 10 Amps. In some implementations, the control component may be configured to provide up to approximately 96% efficiency of the power source. In some implementations, the control component may be configured to establish a time to reach temperature of less than approximately 10 seconds. In some implementations, the inhalable substance medium may include tobacco or a tobacco-derived material. In some implementations, at least a portion of the inhalable substance medium may comprise at least one of tobacco-containing beads, tobacco shreds, tobacco strips, pieces of a reconstituted tobacco material, and a tobacco cast sheet. In some implementations, at least a portion of the inhalable substance medium may comprise an extruded structure (with or without a central opening) that includes tobacco or a tobacco-derived material. In some implementations, the aerosol source member may include an overwrap comprising a paper material that surrounds the inhalable substance medium. In some implementations, the aerosol source member may include filter material located proximate the mouth end of the aerosol source member. In some implementations, the mouth end of the aerosol source member may be partially occluded. In some implementations, the control body may further include one or more ventilation openings configured to allow entry of ambient air into the control body.

Some implementations may further comprise a puff-activated switch that actuates current flow from the power source to the heating member. Some implementations may further comprise a manually operated pushbutton that actuates current flow from the power source to the heating member. In some implementations, the power source may comprise a battery. Some implementations may further comprise a current regulating component configured to regulate a previously initiated current flow from the power source to the heating member. In some implementations, the current regulating component may comprise a time-based component. In some implementations, the current regulating component may be configured to stop current to the electrical heating member once a defined temperature has been achieved. In some implementations, the current regulating component may be configured to cycle the current to the electrical heating member off and on once a defined temperature has been achieved so as to maintain the defined temperature for a defined period of time. In some implementations, the aerosol source member may defines an outer surface, and fluid passage along the length of the aerosol source member may be substantially limited to passage within the aerosol source member.

In another implementation, the aerosol delivery device may comprise a substantially tubular control body having a closed distal end and an open engaging end, a heating member, a control component located within the control body and configured to control the heating member, a power source located within the control body and configured to provide power to the control component, and a substantially cylindrical removable aerosol source member that includes an inhalable substance medium, the aerosol source member being configured to be inserted into the engaging end of the control body and defining a heated end and a mouth end, the heated end configured, when inserted into the control body, to be positioned proximate the heating member, and the mouth end configured to extend beyond the engaging end of the control body. The heating member may be configured to provide heat to at least a portion of the aerosol source member so as to form an inhalable aerosol, the aerosol configured to be drawn through the aerosol source member in response to a draw applied to the mouth end of the inhalable substance medium, and the heating member may comprise a plurality of heater prongs that extend into at least a portion of the engagement end of the control body.

In some implementations, at least a portion of the heating member may be in direct contact with the inhalable substance medium. In some implementations, the control component may be configured to provide an operating current that is at or between a range of approximately 2.5 Amps to approximately 10 Amps. In some implementations, the control component may be configured to provide up to approximately 96% efficiency of the power source. In some implementations, the control component may be configured to establish a time to reach temperature of less than approximately 10 seconds. In some implementations, the inhalable substance medium may include tobacco or a tobacco-derived material. In some implementations, at least a portion of the inhalable substance medium may comprise at least one of tobacco-containing beads, tobacco shreds, tobacco strips, pieces of a reconstituted tobacco material, and a tobacco cast sheet. In some implementations, at least a portion of the inhalable substance medium may comprise an extruded structure (with or without a central opening) that includes tobacco or a tobacco-derived material. In some implementations, the aerosol source member may include an overwrap comprising a paper material that surrounds the inhalable substance medium. In some implementations, the aerosol source member may include filter material located proximate the mouth end of the aerosol source member. In some implementations, the mouth end of the aerosol source member may be partially occluded. In some implementations, the control body may further include one or more ventilation openings configured to allow entry of ambient air into the control body.

Some implementations may further comprise a puff-activated switch that actuates current flow from the power source to the heating member. Some implementations may further comprise a manually operated pushbutton that actuates current flow from the power source to the heating member. In some implementations, the power source may comprise a battery. Some implementations may further comprise a current regulating component configured to regulate a previously initiated current flow from the power source to the heating member. In some implementations, the current regulating component may comprise a time-based component. In some implementations, the current regulating component may be configured to stop current to the electrical heating member once a defined temperature has been achieved. In some implementations, the current regulating component may be configured to cycle the current to the electrical heating member off and on once a defined temperature has been achieved so as to maintain the defined temperature for a defined period of time. In some implementations, the aerosol source member may define an outer surface, and fluid passage along the length of the aerosol source member is substantially limited to passage within the aerosol source member.

These and other features, aspects, and advantages of the present disclosure will be apparent from a reading of the following detailed description together with the accompanying drawings, which are briefly described below.

BRIEF DESCRIPTION OF THE DRAWINGS

Figure 1:
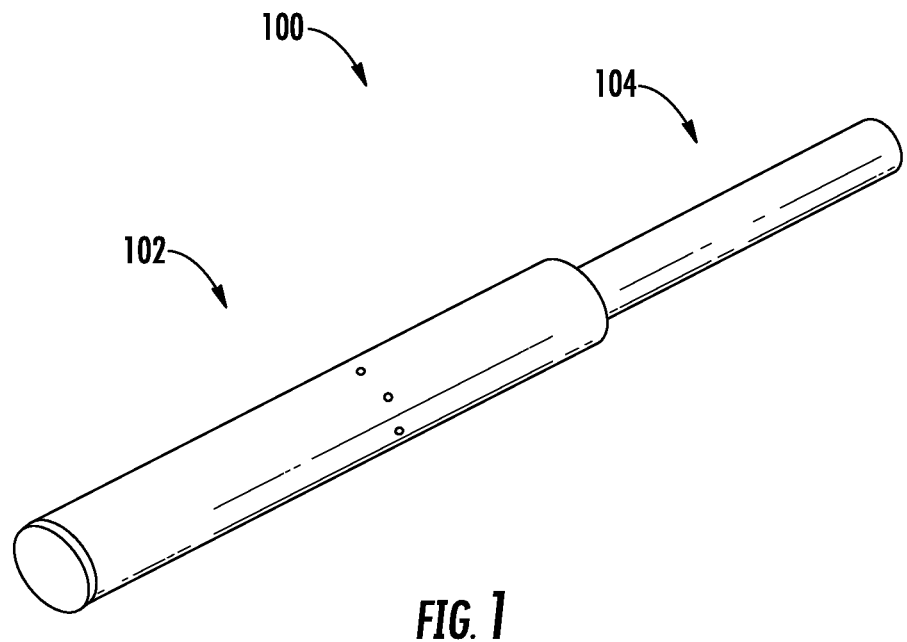
Figure 2:
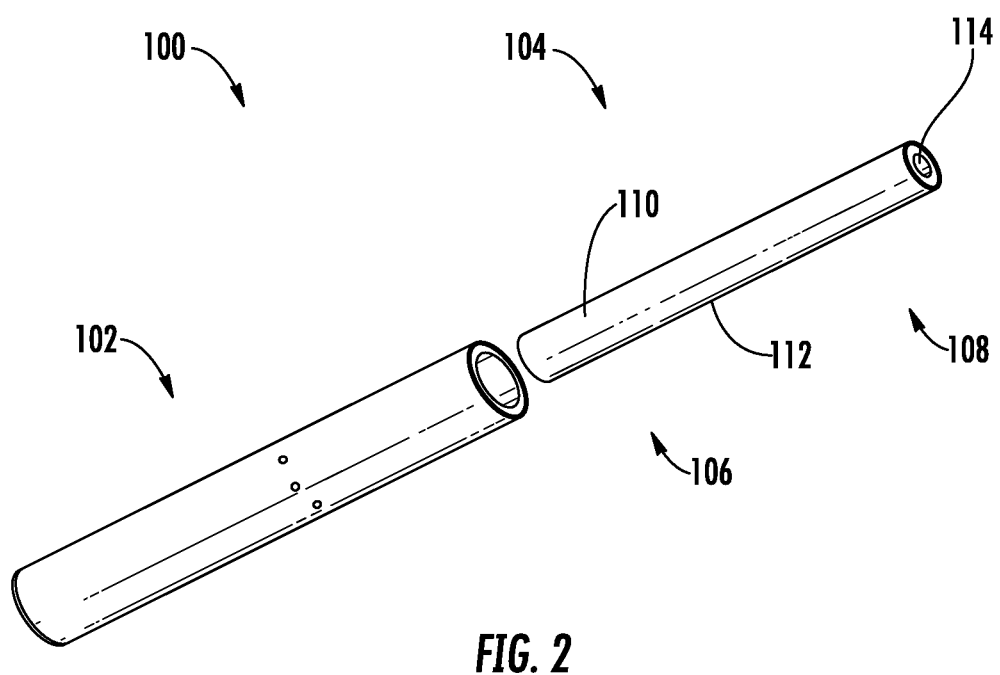
Figure 3:
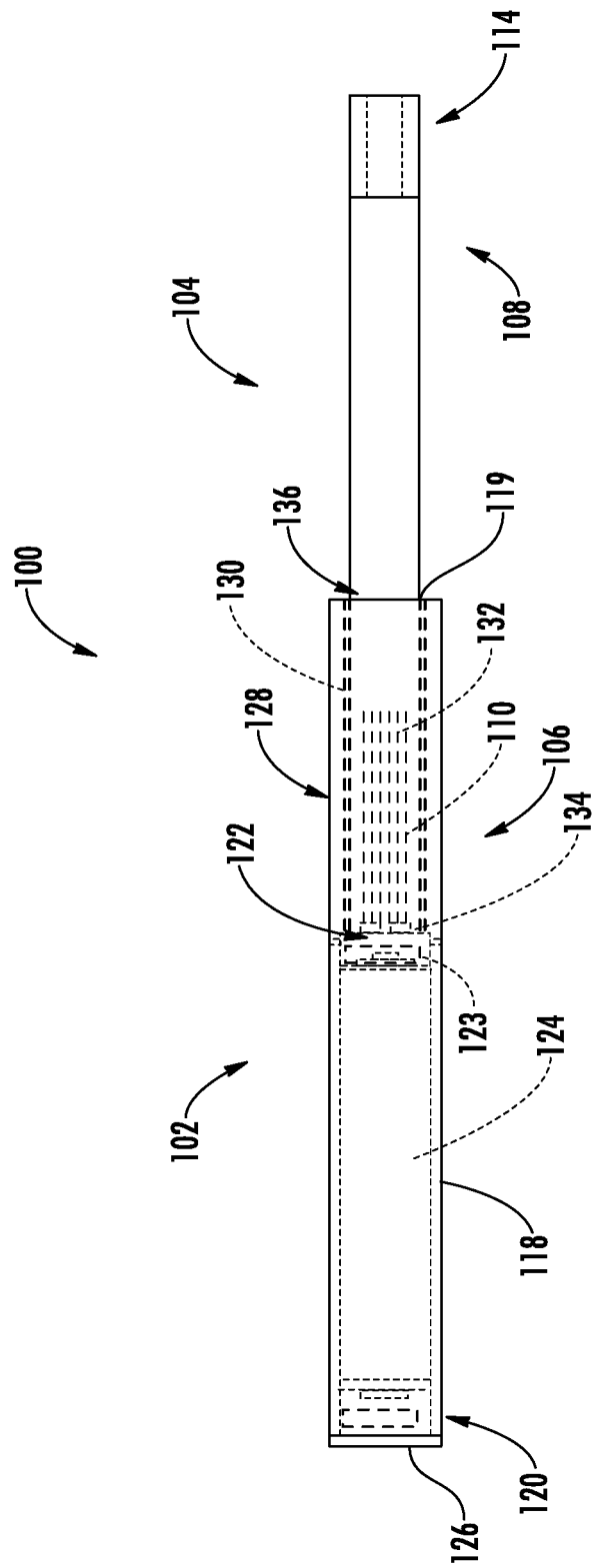
Figure 4:
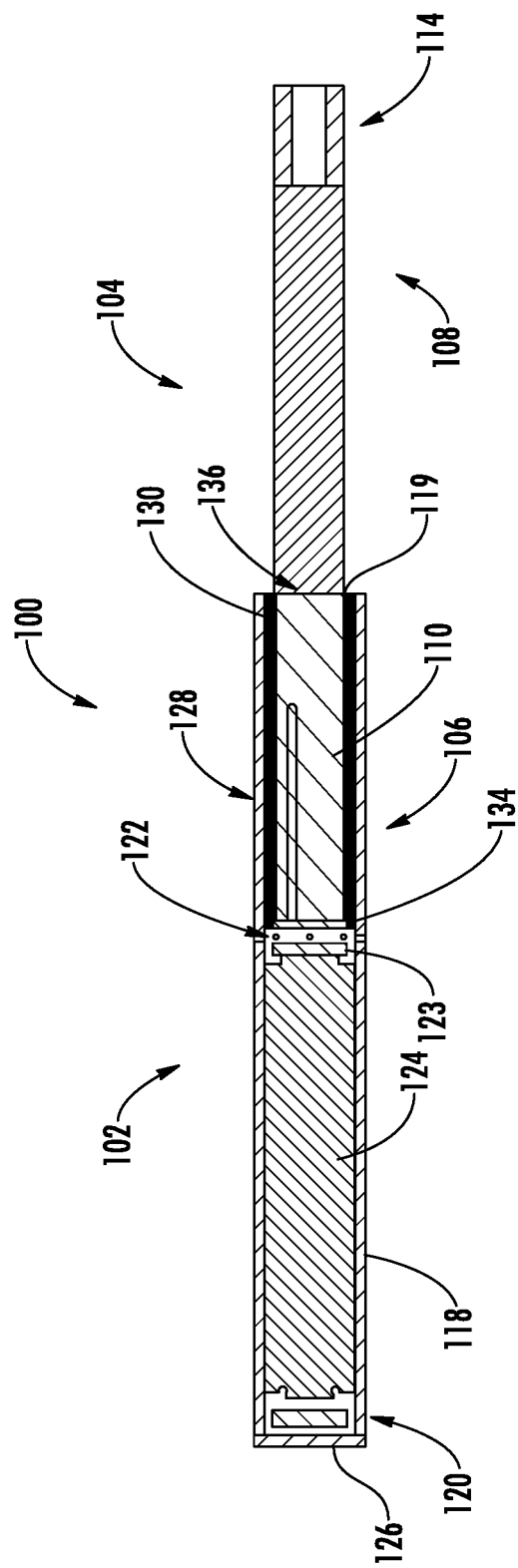
Figure 5:
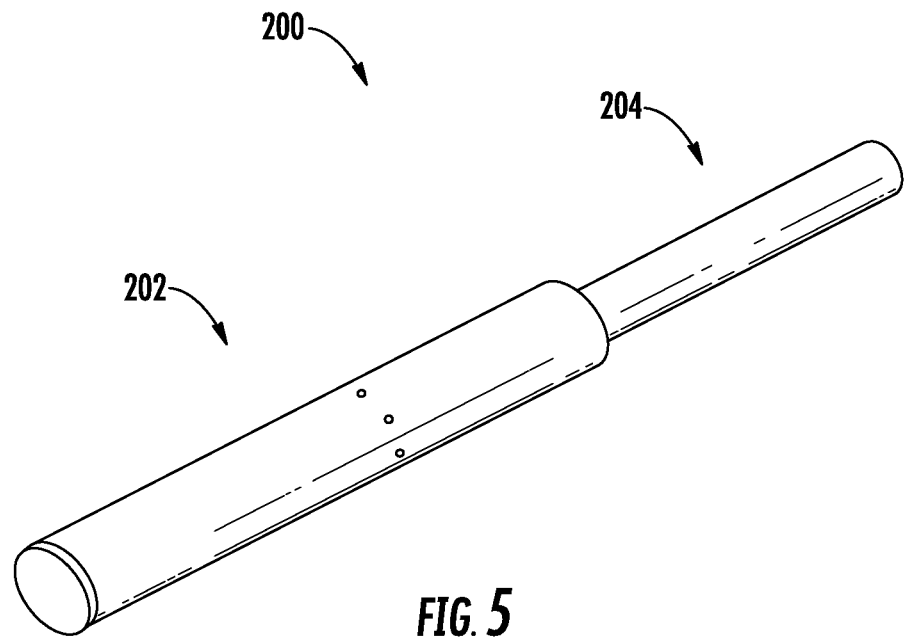
Figure 6:
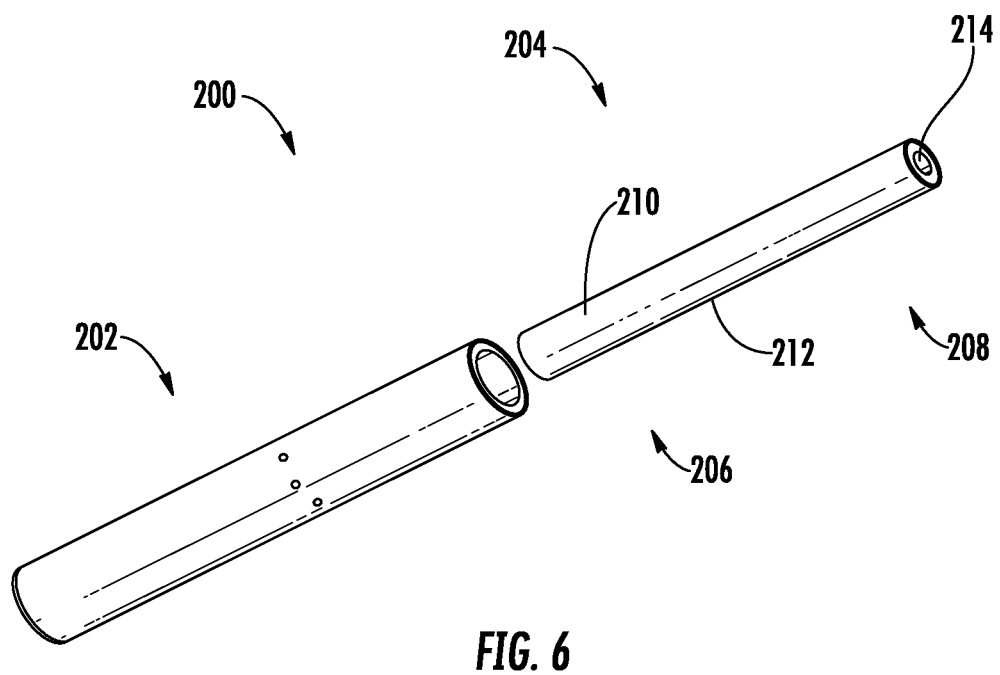
Figure 7:
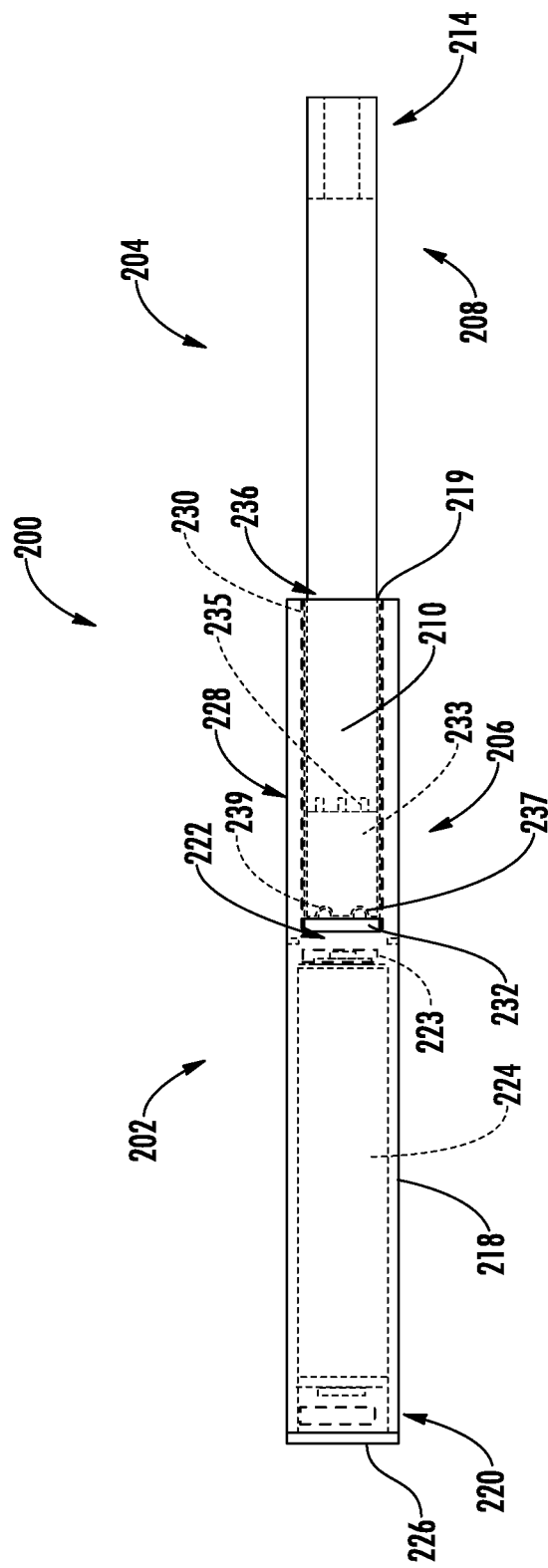
Figure 8:
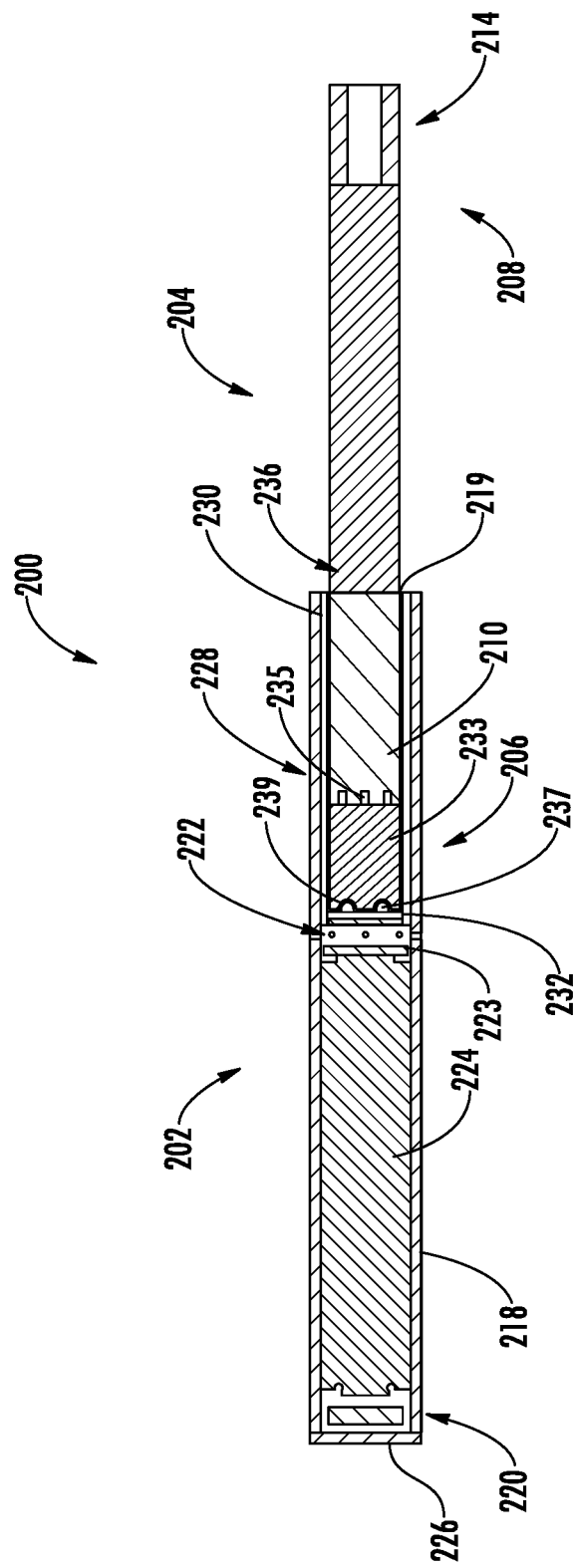
Figure 9:
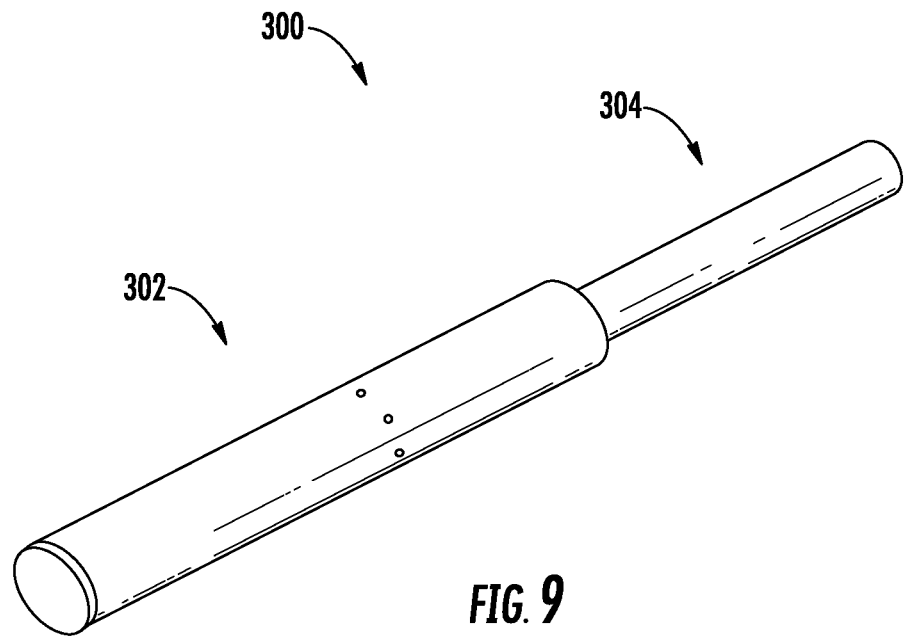
Figure 10:
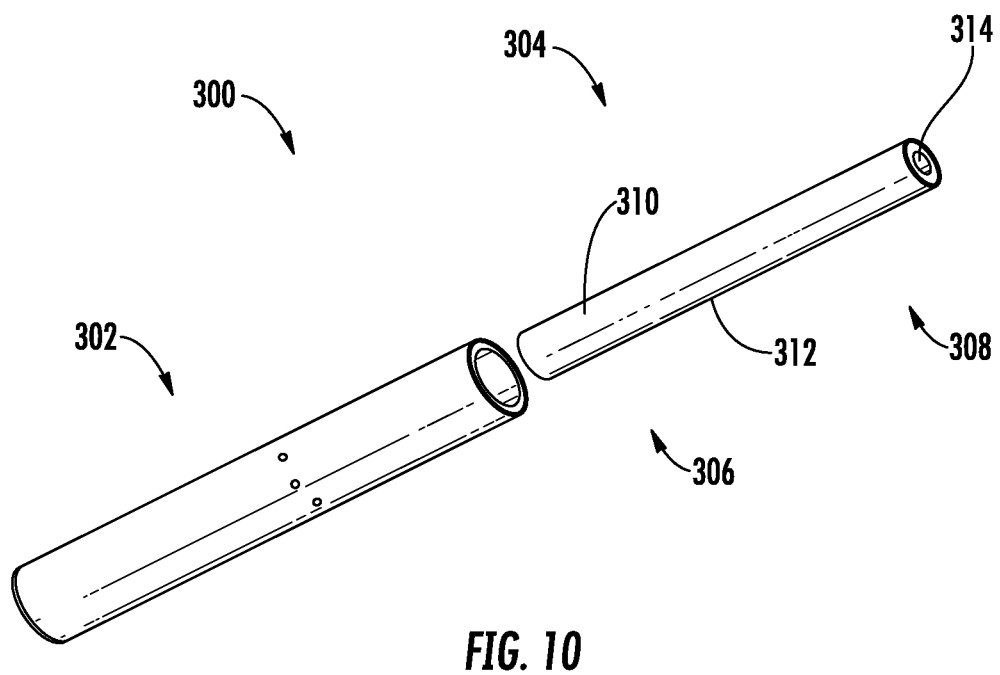
Figure 11:
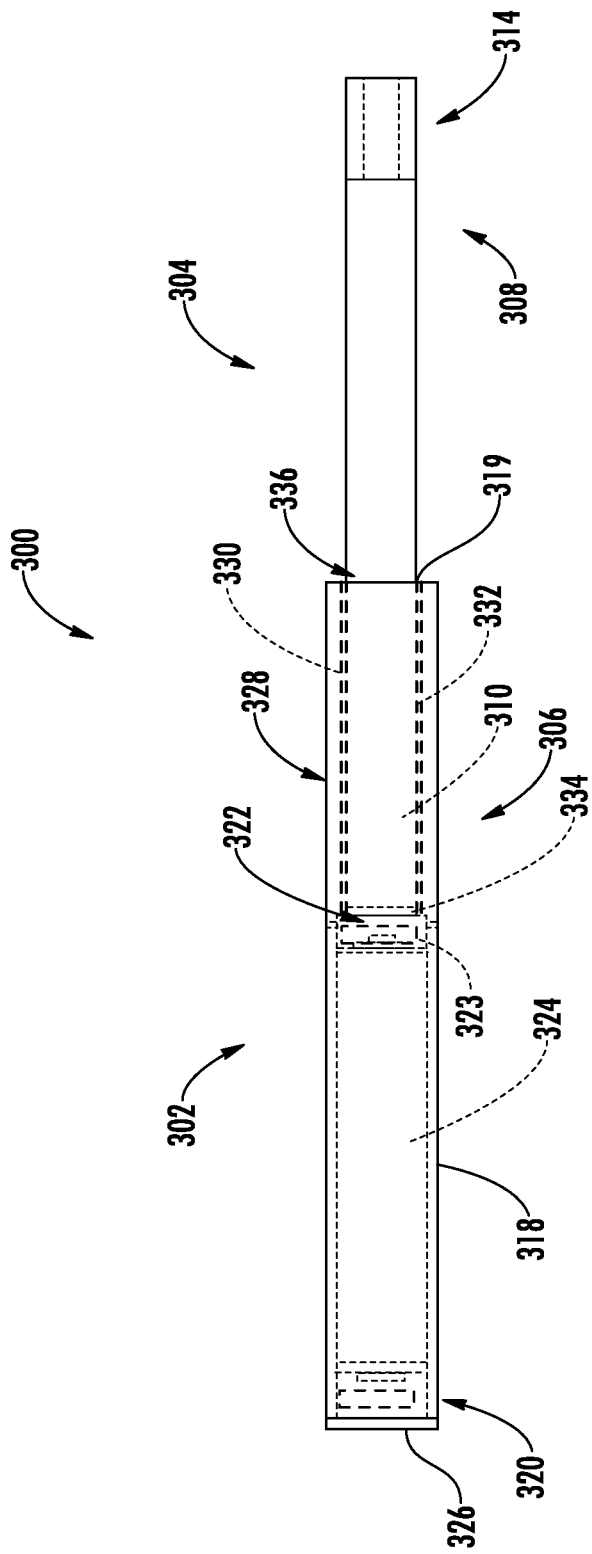
Figure 12:
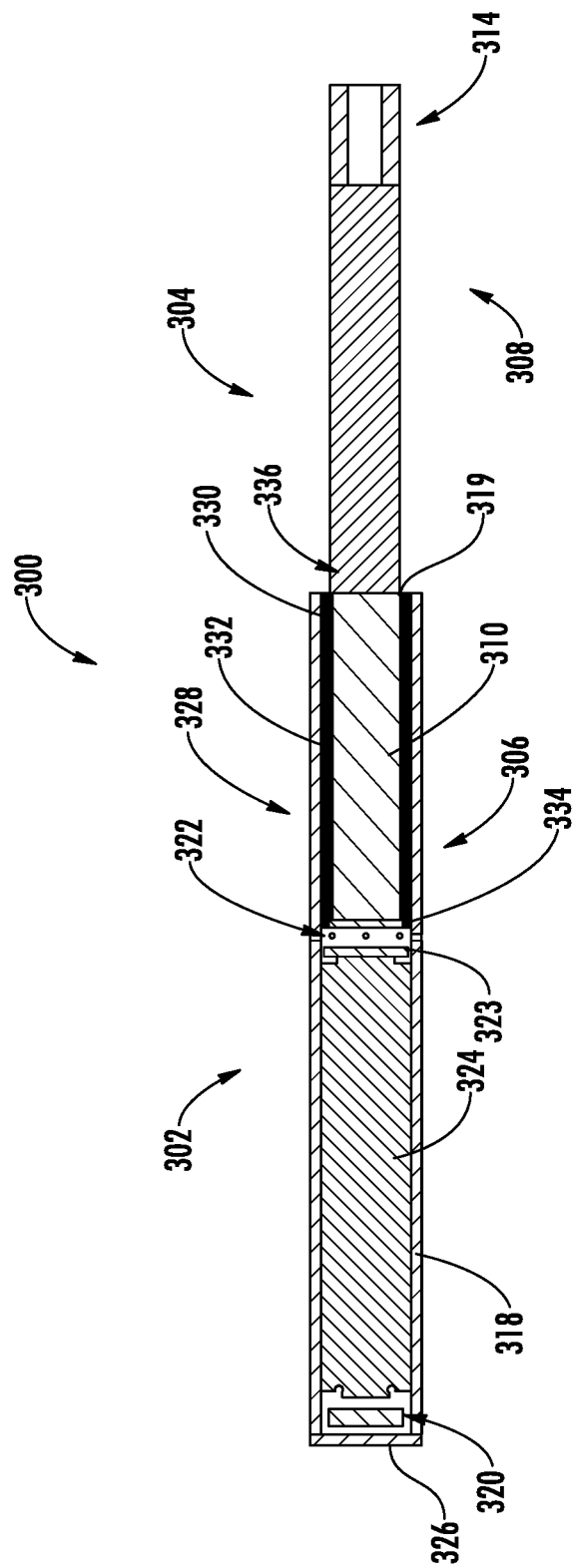
Figure 13:
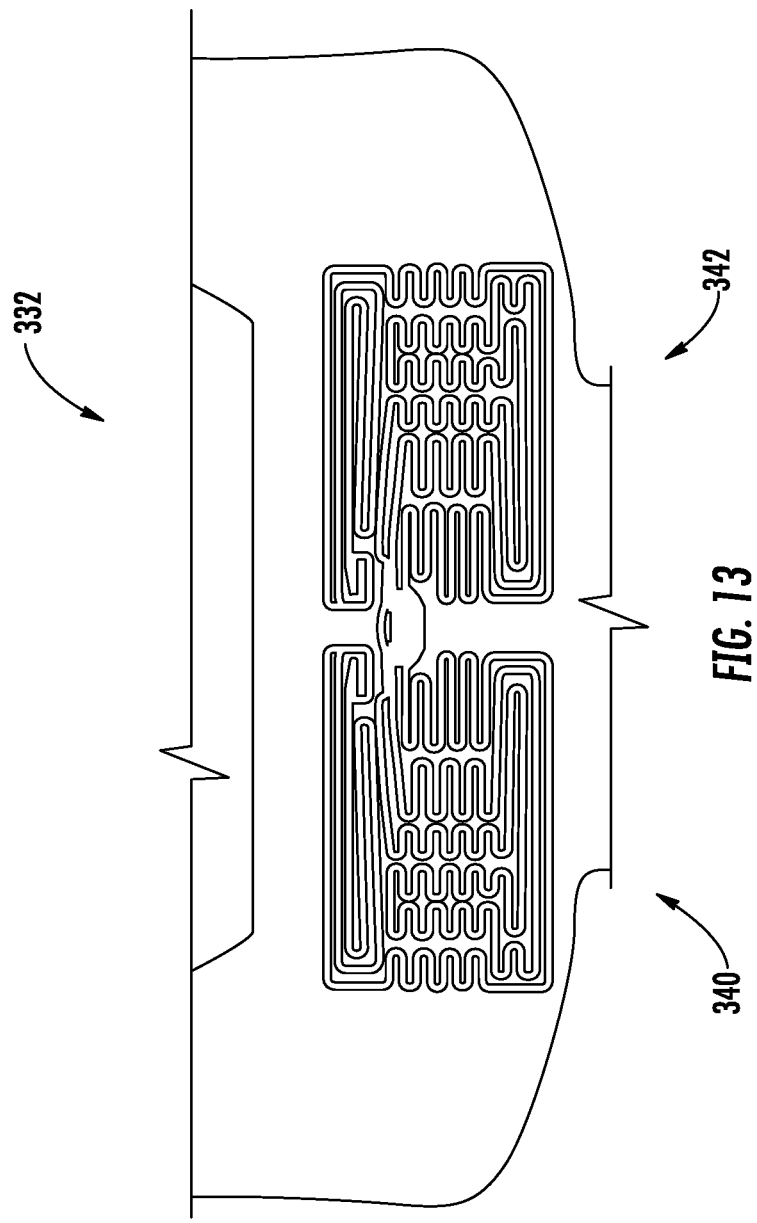
Figure 14:
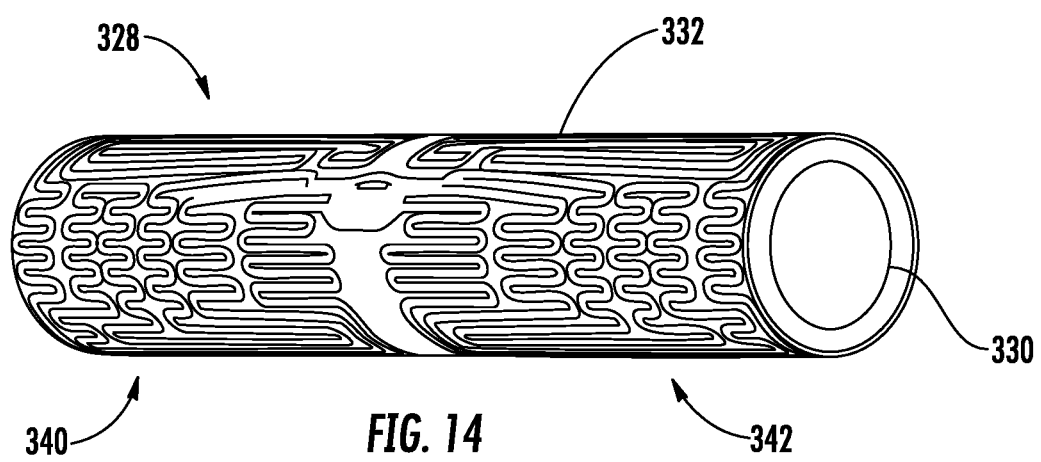
Figure 15:
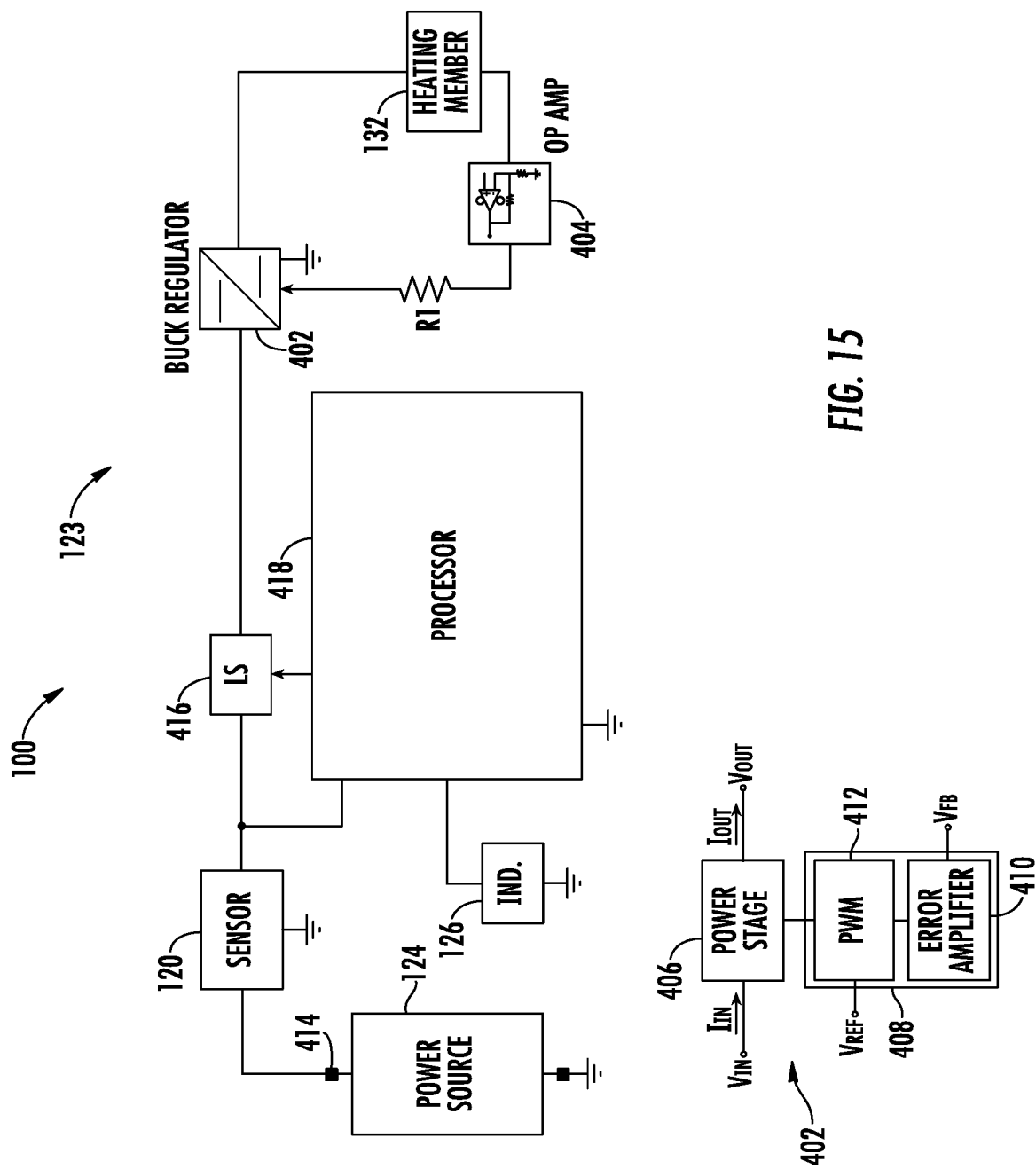

Having thus described the present disclosure in the foregoing general terms, reference will now be made to the accompanying drawings, which are not necessarily drawn to scale, and wherein:

FIG. 1 illustrates a perspective view of an aerosol delivery device comprising a control body and an aerosol source member, wherein the aerosol source member and the control body are coupled to one another according to an example implementation of the present disclosure;

FIG. 2 illustrates a perspective view of the aerosol delivery device of FIG. 1 wherein the aerosol source member and the control body are decoupled from one another according to an example implementation of the present disclosure;

FIG. 3 illustrates a front schematic view of an aerosol delivery device according to an example implementation of the present disclosure;

FIG. 4 illustrates a sectional view through the aerosol delivery device of FIG. 3;

FIG. 5 illustrates a perspective view of an aerosol delivery device comprising a control body and an aerosol source member, wherein the aerosol source member and the control body are coupled to one another according to another example implementation of the present disclosure;

FIG. 6 illustrates a perspective view of the aerosol delivery device of FIG. 5 wherein the aerosol source member and the control body are decoupled from one another according to an example implementation of the present disclosure;

FIG. 7 illustrates a front schematic view of an aerosol delivery device according to an example implementation of the present disclosure;

FIG. 8 illustrates a sectional view through the aerosol delivery device of FIG. 7;

FIG. 9 illustrates a perspective view of an aerosol delivery device comprising a control body and an aerosol source member, wherein the aerosol source member and the control body are coupled to one another according to another example implementation of the present disclosure;

FIG. 10 illustrates a perspective view of the aerosol delivery device of FIG. 9 wherein the aerosol source member and the control body are decoupled from one another according to an example implementation of the present disclosure;

FIG. 11 illustrates a front schematic view of a support cylinder according to an example implementation of the present disclosure;

FIG. 12 illustrates a sectional view through the support cylinder of FIG. 11;

FIG. 13 illustrates a top view of the heating member of an example implementation of the present disclosure;

FIG. 14 illustrates a perspective view of a heating assembly incorporating the heating member of FIG. 13 according to an example implementation of the present disclosure; and FIG. 15 depicts circuit diagrams of the aerosol delivery device according to various example implementations of the present disclosure.

DETAILED DESCRIPTION

The present disclosure will now be described more fully hereinafter with reference to example implementations thereof. These example implementations are described so that this disclosure will be thorough and complete, and will fully convey the scope of the present disclosure to those skilled in the art. Indeed, the present disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes," or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms may be interchangeable. Thus, for simplicity, the terms as used to describe the present disclosure are understood to be interchangeable unless stated otherwise.

Aerosol delivery devices of the present disclosure generally include a number of components provided within an outer body or shell, which may be referred to as a housing. The overall design of the outer body or shell may vary, and the format or configuration of the outer body that may define the overall size and shape of the aerosol delivery device may vary. Typically, an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the aerosol delivery device are contained within one housing. Alternatively, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing aerosol source member). More specific formats, configurations and arrangements of components within the single housing type of unit or within a multi-piece separable housing type of unit will be evident in light of the further disclosure provided herein. Additionally, various aerosol delivery device designs and component arrangements may be appreciated upon consideration of the commercially available electronic aerosol delivery devices.

As will be discussed in more detail below, aerosol delivery devices of the present disclosure comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component), and an aerosol source member that includes an inhalable substance medium capable of yielding an aerosol upon application of sufficient heat. In various implementations, the aerosol source member may include a mouth end or tip configured to allow drawing upon the aerosol delivery device for aerosol inhalation (e.g., a defined airflow path through the article such that aerosol generated can be withdrawn therefrom upon draw).

Alignment of the components within the aerosol delivery device of the present disclosure may vary across various implementations. In some implementations, the inhalable substance medium may be positioned proximate a heating member so as to maximize aerosol delivery to the user. Other configurations, however, are not excluded. Generally, the heating member may be positioned sufficiently near the inhalable substance medium so that heat from the heating member can volatilize the inhalable substance medium (as well as, in some implementations, one or more flavorants, medicaments, or the like that may likewise be provided for delivery to a user) and form an aerosol for delivery to the user. When the heating member heats the inhalable substance medium, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device of various implementations may incorporate a battery or other electrical power source to provide current flow sufficient to provide various functionalities to the aerosol delivery device, such as powering of a heating member, powering of control systems, powering of indicators, and the like. As will be discussed in more detail below, the power source may take on various implementations. Preferably, the power source is able to deliver sufficient power to rapidly activate the heating source to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

As indicated above, the aerosol delivery device may include at least one control component. A suitable control component may include a number of electronic components, and in some examples may be formed of a printed circuit board (PCB). In some examples, the electronic components include processing circuitry configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like. Additionally or alternatively, the control component may include one or more input/output peripherals may be coupled to or integrated with the processing circuitry, such as a communication interface to enable wireless communication with one or more networks, computing devices or other appropriately-enabled devices.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device may also be appreciated upon consideration of the commercially available electronic aerosol delivery devices.

In this regard, FIG. 1 illustrates an aerosol delivery device 100 according to an example implementation of the present disclosure. The aerosol delivery device 100 may include a control body 102 and an aerosol source member 104. In various implementations, the aerosol source member 104 and the control body 102 may be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like.

In various implementations, the aerosol delivery device 100 according to the present disclosure may have a variety of overall shapes, including, but not limited to an overall shape that may be defined as being substantially rod-like or substantially tubular shaped or substantially cylindrically shaped. In the implementations of FIGS. 1-4, the device 100 has a substantially round cross-section; however, other cross-sectional shapes (e.g., oval, square, triangle, etc.) also are encompassed by the present disclosure. Such language that is descriptive of the physical shape of the article may also be applied to the individual components thereof, including the control body 102 and the aerosol source member 104. In other implementations, the control body may take another hand-held shape, such as a small box shape.

In specific implementations, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 104 may comprise a single-use device. A similar single use component for use with a control body is disclosed in U.S. Pat. No. 8,910,639 to Chang et al., which is incorporated herein by reference in its entirety.

In the depicted implementation, the aerosol source member 104 comprises a heated end 106, which is configured to be inserted into the control body 102, and a mouth end 108, upon which a user draws to create the aerosol. At least a portion of the heated end 106 may include the inhalable substance medium 110. As discussed in more detail below, the inhalable substance medium 110 may comprise tobacco-containing beads, tobacco shreds, tobacco strips, a tobacco cast sheet, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid, semi-solid, or moldable (e.g., extruded) substrate. Representative types of solid and semi-solid inhalable substance medium constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein.

In various implementations, the aerosol source member 104, or a portion thereof, may be wrapped in an overwrap material 112 (see FIG. 2), which may be formed of any material useful for providing additional structure and/or support for the aerosol source member 104. In various implementations, the mouth end 108 of the aerosol source member 104 may include a filter 114, which may be made of a cellulose acetate or polypropylene material. The filter 114 may increase the structural integrity of the mouth end of the aerosol source member, and/or provide filtering capacity, if desired, and/or provide resistance to draw. The overwrap material may comprise a material that resists transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material may incorporate inorganic components. In various implementations, the overwrap may be formed of multiple layers, such as an underlying, bulk layer and an overlying layer, such as a typical wrapping paper in a cigarette. Such materials may include, for example, light-weight "rag fibers" such as flax, hemp, sisal, rice straw, and/or esparto. The overwrap may also include a material typically used in a filter element of a conventional cigarette, such as cellulose acetate. Further, an excess length of the overwrap at the mouth end 108 of the aerosol source member may function to simply separate the inhalable substance medium 110 from the mouth of a consumer or to provide space for positioning of a filter material, as described below, or to affect draw on the article or to affect flow characteristics of the vapor or aerosol leaving the device during draw. Further discussions relating to the configurations for overwrap materials that may be used with the present disclosure may be found in U.S. Pat. No. 9,078,473 to Worm et al., which is incorporated herein by reference in its entirety.

In various implementations other components may exist between the inhalable substance medium 110 and the mouth end 108 of the aerosol source member 104, wherein the mouth end 108 may include a filter 114. For example, in some implementations one or any combination of the following may be positioned between the inhalable substance medium 110 and the mouth end 108 of the aerosol source member 104: an air gap; phase change materials for cooling air; flavor releasing media; ion exchange fibers capable of selective chemical adsorption; aerogel particles as filter medium; and other suitable materials.

As will be discussed in more detail below, the present disclosure employs a conductive heat source to heat the inhalable substance medium. In various implementations, the conductive heat source may comprise a heating assembly that includes a heating member in direct contact with, or in proximity to, the aerosol source member and particularly, the inhalable substance medium of the aerosol source member. The heating assembly or the heating member may be located in the control body and/or the aerosol source member, as will be discussed in more detail below. In some instances, the inhalable substance medium may include a structure in contact with, or a plurality of beads or particles imbedded in, or otherwise part of, the inhalable substance medium that may serve as, or facilitate the function of the heating assembly.

In some devices, the heating member may comprise a resistive heating element. Resistive heating elements may be configured to produce heat when an electrical current is directed therethrough. In various implementations, the heating member may be provided in a variety forms, such as in the form of a foil, a foam, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in proximity to the inhalable substance medium. Alternatively, the heating member may be positioned in contact with a solid or semi-solid inhalable substance medium. Such configurations may heat the inhalable substance medium to produce an aerosol. A variety of conductive substrates that may be usable with the present disclosure are described in U.S. Pat. App. Pub. No. 2013/0255702 to Griffith et al., the disclosure of which is incorporated herein by reference in its entirety. Some non-limiting examples of various heating member configurations include configurations in which a heating member or element is placed in proximity with an aerosol source member. For instance, in some examples, at least a portion of a heating element may surround at least a portion of an aerosol source member. In other examples, one or more heating elements may be positioned adjacent an exterior of an aerosol source member when inserted in a control body. In other examples, at least a portion of a heating element may penetrate at least a portion of an aerosol source member (such as, for example, one or more prongs and/or spikes that penetrate an aerosol source member), when the aerosol source member is inserted into the control body.

FIG. 3 illustrates a front schematic view of an aerosol delivery device 100 according to an example implementation of the present disclosure, and FIG. 4 illustrates a sectional view through the aerosol delivery device 100 of FIG. 3. As illustrated in the figures, the aerosol delivery device 100 of this example implementation includes a heating assembly 128 that includes a heating member 132, in the form of a plurality of heater prongs, in direct contact with the inhalable substance medium 110. In particular, the control body 102 of the depicted implementation comprises a housing 118 that includes an opening 119 defined in an engaging end thereof. The control body 102 also includes a flow sensor 120 (e.g., a puff sensor or pressure switch), a control component 123 (e.g., processing circuitry, individually or as part of a microcontroller, a printed circuit board (PCB) that includes a microprocessor and/or microcontroller, etc.), a power source 124 (e.g., a battery, which may be rechargeable, and/or a rechargeable supercapacitor), and an end cap that includes an indicator 126 (e.g., a light emitting diode (LED)). In one implementation, the indicator 126 may comprise one or more light emitting diodes, quantum dot-based light emitting diodes or the like. The indicator 126 may be in communication with the control component 123 and be illuminated, for example, when a user draws on the aerosol source member 104, when coupled to the control body 102, as detected by the flow sensor 120.

Other indices of operation are also encompassed by the present disclosure. For example, visual indicators of operation also include changes in light color or intensity to show progression of the smoking experience. Tactile indicators of operation and sound indicators of operation similarly are encompassed by the present disclosure. Moreover, combinations of such indicators of operation also are suitable to be used in a single smoking article. According to another aspect, the device may include one or more indicators or indicia, such as, for example, a display configured to provide information corresponding to the operation of the smoking article such as, for example, the amount of power remaining in the power source, progression of the smoking experience, indication corresponding to activating a heat source, and/or the like. Examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties. With respect to the flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

Still further components may be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. U.S. Pat. App. Pub. No. 2017-0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

Referring back to FIGS. 3 and 4, the control body 102 of the depicted implementation includes a heating assembly 128 configured to heat the inhalable substance medium 110 of the aerosol source member 104. Although the heating assembly of various implementations of the present disclosure may take a variety of forms, in the particular implementation depicted in FIGS. 3 and 4, the heating assembly 128 comprises an outer cylinder 130 and a heating member 132, which in this implementation comprises a plurality of heater prongs that extend from a receiving base 134. In the depicted implementation, the outer cylinder 130 comprises a double-walled vacuum tube constructed of stainless steel so as to maintain heat generated by the heater prongs 132 within the outer cylinder 130, and more particularly, maintain heat generated by heater prongs 132 within the inhalable substance medium 110. In various implementations, the heater prongs 132 may be constructed of one or more conductive materials, including, but not limited to, copper, aluminum, platinum, gold, silver, iron, steel, brass, bronze, graphite, or any combination thereof.

As illustrated, the heating assembly 128 may extend proximate an engagement end of the housing 118, and may be configured to substantially surround a portion of the heated end 106 of the aerosol source member 104 that includes the inhalable substance medium 110. In such a manner, the heating assembly 128 may define a generally tubular configuration. As illustrated in FIGS. 3 and 4, the plurality of heater prongs 132 is surrounded by the outer cylinder 130 to create a receiving chamber 136. In such a manner, in various implementations the outer cylinder 130 may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 128 may be combined with, packaged with, and/or integral with (e.g., embedded within) the inhalable substance medium 110. For example, in some implementations the inhalable substance medium may be formed of a material as described above and may include one or more conductive materials mixed therein. In some of these implementations, contacts may be connected directly to the inhalable substance medium such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the inhalable substance medium. Because of the presence of the conductive material in the inhalable substance medium, the application of power from the electrical energy source to the inhalable substance medium allows electrical current to flow and thus produce heat from the conductive material. Thus, in some implementations the heating member may be described as being integral with the inhalable substance medium. As a non-limiting example, graphite or other suitable, conductive material may be mixed with, embedded in, or otherwise present directly on or within the material forming the inhalable substance medium to make the heating member integral with the medium.

As noted above, in the illustrated implementation, the outer cylinder 130 may also serve to facilitate proper positioning of the aerosol source member 104 when the aerosol source member 104 is inserted into the housing 118. In various implementations, the outer cylinder 130 of the heating assembly 128 may engage an internal surface of the housing 118 to provide for alignment of the heating assembly 128 with respect to the housing 118. Thereby, as a result of the fixed coupling between the heating assembly 128, a longitudinal axis of the heating assembly 128 may extend substantially parallel to a longitudinal axis of the housing 118. In particular, the support cylinder 130 may extend from the opening 119 of the housing 118 to the receiving base 134 to create the receiving chamber 136. In the illustrated implementation, an inner diameter of the outer cylinder 130 may be slightly larger than or approximately equal to an outer diameter of a corresponding aerosol source member 104 (e.g., to create a sliding fit) such that the outer cylinder 130 is configured to guide the aerosol source member 104 into the proper position (e.g., lateral position) with respect to the control body 102.

In the illustrated implementation, the control body 102 is configured such that when the aerosol source member 104 is inserted into the control body 102, the heater prongs 132 are located in the approximate radial center of at least a portion of the inhalable substance medium 110 of the heated end 106 of the aerosol source member 104. In such a manner, when used in conjunction with a solid or semi-solid inhalable substance medium 110, the heater prongs 132 may be in direct contact with the inhalable substance medium 110. In other implementations, such as when used in conjunction with an extruded inhalable substance medium that defines a tube structure, the heater prongs 132 may be located inside of a cavity defined by an inner surface of the extruded tube structure, and would not contact the inner surface of the extruded tube structure.

Referring back to FIGS. 3 and 4, during use, the consumer initiates heating of the heating assembly 128, and in particular, the heating prongs 132 that are adjacent the inhalable substance medium 110 (or a specific layer thereof). Heating of the inhalable substance medium 110 releases the inhalable substance within the aerosol source member 104 so as to yield the inhalable substance. When the consumer inhales on the mouth end 108 of the aerosol source member 104, air is drawn into the aerosol source member 104 through openings or apertures 122 in the control body 102. The combination of the drawn air and the released inhalable substance is inhaled by the consumer as the drawn materials exit the mouth end 108 of the aerosol source member 104. In some implementations, to initiate heating, the consumer may manually actuate a pushbutton or similar component that causes the heating member of the heating assembly to receive electrical energy from the battery or other energy source. The electrical energy may be supplied for a predetermined length of time or may be manually controlled. In some implementations, flow of electrical energy does not substantially proceed in between puffs on the device (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 120. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 104 may be removed from the control body 102 and discarded. In some implementations, further sensing elements, such as capacitive sensing elements and other sensors, may be used as discussed in U.S. patent application Ser. No. 15/707,461 to Phillips et al., which is incorporated herein by reference in its entirety.

In various implementations, the aerosol source member 104 may be formed of any material suitable for forming and maintaining an appropriate conformation, such as a tubular shape, and for retaining therein an inhalable substance medium 110. In some implementations, the aerosol source member 104 may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating member, as further discussed herein.

While in some implementations, a heat resistant polymer may be used, in other implementations, the aerosol source member 104 may be formed from paper, such as a paper that is substantially straw-shaped. As further discussed herein, the aerosol source member 104 may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the inhalable substance medium. The aerosol source member 104, when formed of a single layer, may have a thickness that preferably is about 0.2 mm to about 7.5 mm, about 0.5 mm to about 4.0 mm, about 0.5 mm to about 3.0 mm, or about 1.0 mm to about 3.0 mm. Further exemplary types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

As discussed above, the aerosol source member 104 includes an inhalable substance medium 110 proximate a heated end 106 of the member 104. In various implementations, the inhalable substance medium 110 may be any material that, when heated, releases an inhalable substance, such as a flavor-containing substance. In the implementations of FIGS. 3-4, the inhalable substance medium 110 comprises a solid substrate that includes the inhalable substance. In various implementations, the inhalable substance specifically may be a tobacco component or a tobacco-derived material (i.e., a material that is found naturally in tobacco that may be isolated directly from the tobacco or synthetically prepared). For example, the inhalable substance medium may comprise tobacco extracts or fractions thereof combined with an inert substrate. The inhalable substance medium may further comprise unburned tobacco or a composition containing unburned tobacco that, when heated to a temperature below its combustion temperature, releases an inhalable substance. In some implementations, the inhalable substance medium may comprise tobacco condensates or fractions thereof (i.e., condensed components of the smoke produced by the combustion of tobacco, leaving flavors and, possibly, nicotine). Tobacco materials useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT Pat. App. Pub. No. WO 02/37990 to Bereman; and Bombick et al., Fund. Appl. Toxicol., 39, p. 11-17 (1997); which are incorporated herein by reference. Further exemplary tobacco compositions that may be useful in a smoking device, including according to the present disclosure, are disclosed in U.S. Pat. No. 7,726,320 to Robinson et al., which is incorporated herein by reference in its entirety.

Still further, the inhalable substance medium may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the inhalable substance medium may comprise a blend of flavorful and aromatic tobaccos in cut filler form. In another aspect, the inhalable substance medium may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety.

In some implementations, the inhalable substance medium may include tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

In some implementations, other flame/burn retardant materials and additives may be included within the inhalable substance medium and my include organo-phosphorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the inhalable substance medium and/or other components (whether alone or in combination with each other and/or other materials), the desirable properties are preferably provided without undesirable off-gassing or melting-type behavior. Additional flavorants, flavoring agents, additives, and other possible enhancing constituents are described in U.S. patent application Ser. No. 15/707,461 to Phillips et al., which is incorporated herein by reference in its entirety.

In addition to the inhalable substance (e.g., flavors, nicotine, or pharmaceuticals generally), the inhalable substance medium may comprise one or more aerosol-forming or vapor-forming materials, such as a polyhydric alcohol (e.g., glycerin, propylene glycol, or a mixture thereof) and/or water. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and Chemical and Biological Studies on New Cigarette Prototypes that Heat Instead of Burn Tobacco, R. J. Reynolds Tobacco Company Monograph (1988); which are incorporated herein by reference. In some aspects, the inhalable substance medium produces a visible aerosol upon the application of sufficient heat thereto (and cooling with air, if necessary), and the aerosol delivery component produces an aerosol that is smoke-like. In other aspects, the aerosol delivery component produces an aerosol that is substantially non-visible but is recognized as present by other characteristics, such as flavor or texture. Thus, the nature of the produced aerosol is variable depending upon the specific components of the aerosol delivery component. The aerosol delivery component is chemically simple relative to the chemical nature of the smoke produced by burning tobacco.

Further tobacco materials, such as a tobacco aroma oil, a tobacco essence, a spray dried tobacco extract, a freeze dried tobacco extract, tobacco dust, or the like may be combined with the vapor-forming or aerosol-forming material. It is also understood that the inhalable substance itself may be in a form whereby, upon heating, the inhalable substance is released as a vapor, aerosol, or combination thereof. In other implementations, the inhalable substance may not necessarily release in a vapor or aerosol form, but the vapor-forming or aerosol-forming material that may be combined therewith can form a vapor or aerosol upon heating and function essentially as a carrier for the inhalable substance itself. Thus, the inhalable substance may be characterized as being coated on a substrate, as being absorbed in a substrate, as being adsorbed in a substrate, or as being a natural component of the substrate (i.e., the material forming the substrate, such as a tobacco or a tobacco-derived material). Likewise, an aerosol-forming or vapor-forming material may be similarly characterized. In certain implementations, the inhalable substance medium may particularly comprise a substrate with the inhalable substance and a separate aerosol forming material included therewith. As such, in use, the substrate may be heated, and the aerosol forming material may be volatilized into a vapor form taking with it the inhalable substance. In a specific example, the inhalable substance medium may comprise a solid substrate with a slurry of tobacco and an aerosol-forming material and/or vapor-forming material coated thereon or absorbed or adsorbed therein. The substrate component may be any material that does not combust or otherwise degrade at the temperatures described herein that the heating member achieves to facilitate release of the inhalable substance. For example, a paper material may be used, including a tobacco paper (e.g., a paper-like material comprising tobacco fibers and/or reconstituted tobacco). Thus, in various implementations, the inhalable substance medium may be characterized as comprising the inhalable substance, alternately as comprising the inhalable substance and a separate aerosol-former or vapor-former, alternately as comprising the inhalable substance and a substrate, or alternately as comprising the inhalable substance medium, the separate aerosol-former or vapor-former, and the substrate. Thus, the substrate may contain one or both of the inhalable substance and the aerosol-former or vapor-former.

In some aspects of the present disclosure, the inhalable substance medium may be configured as an extruded material, as described in U.S. Pat. App. Pub. No. 2012/0042885 to Stone et al., which is incorporated herein by reference in its entirety. In still another aspects, the inhalable substance medium may be configured as an extruded structure and/or substrate that includes, or is essentially comprised of tobacco, tobacco-related material, glycerin, water, and/or a binder material, although certain formulations exclude the binder material. In various implementations, the binder material may be any binder material commonly used for tobacco formulations including, for example, carboxymethyl cellulose (CMC), gum (e.g. guar gum), xanthan, pullulan, and/or an alginate. According to some aspects, the binder material included in the aerosol delivery component may be configured to substantially maintain a structural shape and/or integrity of the aerosol delivery component. Various representative binders, binder properties, usages of binders, and amounts of binders are set forth in U.S. Pat. No. 4,924,887 to Raker et al., which is incorporated herein by reference in its entirety.

In some implementations, the inhalable substance medium is further configured to substantially maintain its structure throughout the aerosol-generating process. That is, the inhalable substance medium is configured to substantially maintain its shape (i.e., the aerosol delivery component does not continually deform under an applied shear stress) throughout the aerosol-generating process. Although in some implementations the inhalable substance medium component may include liquids and/or some moisture content, in some implementations the inhalable substance medium is configured to remain substantially solid throughout the aerosol-generating process and substantially maintain its structural integrity throughout the aerosol-generating process. Exemplary tobacco and/or tobacco related materials suitable for a substantially solid aerosol delivery component are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are all incorporated herein in their entirety by reference respectively.

In yet another aspect, the inhalable substance medium may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents.

In another aspect, the inhalable substance medium may include a plurality of microcapsules, beads, granules, and/or the like having a tobacco-related material. For example, a representative microcapsule may generally be spherical in shape, and may have an outer cover or shell that contains a liquid center region of a tobacco-derived extract and/or the like. In some aspects, the aerosol delivery component may include a plurality of microcapsules each formed into a hollow cylindrical shape. In one aspect, the aerosol delivery component may include a binder material configured to maintain the structural shape and/or integrity of the plurality of microcapsules formed into the hollow cylindrical shape. Various other configurations and components that may be included in the inhalable substance medium of the present disclosure are described in in U.S. Pat. No. 9,078,473 to Worm et al., which is incorporated herein by reference in its entirety. In another aspect, the inhalable substance medium may include one or more heat conducting materials. Examples of substrate portions that include heat conducting materials are described in U.S. patent application Ser. No. 15/905,320 to Sebastian, titled: Heat Conducting Substrate For Electrically Heated Aerosol Delivery Device, filed on Feb. 26, 2018, which is incorporated herein by reference.

In various implementations, tensioning of the inhalable substance medium may be included to provide for specific performance of the device of the present disclosure. As otherwise described herein, it may be beneficial for the inhalable substance medium to have a relatively small thickness such that heat is efficiently transferred, particularly when substrates, such as paper, that exhibit relatively low heat transfer are used. Substrates of small thickness, however, can have relatively low strength in certain dimensions while exhibiting relatively high strength in other dimensions. For example, thin paper, in tension, exhibits high strength relative to the strength of the same paper in compression. Tensioning also can facilitate direct contact of the heating member to the surface of the inhalable substance medium to be heated (including a substrate that is used or a vapor barrier that may be present). A variety of other configurations for the inhalable substance medium of an aerosol source member may be found in the discussion of similar configurations found in U.S. Pat. No. 9,078,473 to Worm et al., which is incorporated herein by reference in its entirety.

Referring back to FIGS. 3 and 4, the heated end 106 of the aerosol source member 104 is sized and shaped for insertion into the control body 102. In various implementations, the receiving chamber 136 of the control body 102 may be characterized as being defined by a wall with an inner surface and an outer surface, the inner surface defining the interior volume of the receiving chamber 136. For example, in the depicted implementations, the outer cylinder 130 defines an inner surface defining the interior volume of the receiving chamber 136. Thus, the largest outer diameter (or other dimension depending upon the specific cross-sectional shape of the implementations) of the aerosol source member 104 may be sized to be less than the inner diameter (or other dimension) at the inner surface of the wall of the open end of the receiving chamber 136 in the control body 102. In some implementations, the difference in the respective diameters may be sufficiently small so that the aerosol source member fits snugly into the receiving chamber 136, and frictional forces prevent the aerosol source member 104 from being moved without an applied force. On the other hand, the difference may be sufficient to allow the aerosol source member 104 to slide into or out of the receiving chamber 136 without requiring undue force.

In some implementations, the overall size of the aerosol delivery device 100 may take on a size that is comparative to a cigarette or cigar shape. Thus, the device may have a diameter of about 5 mm to about 25 mm, about 5 mm to about 20 mm, about 6 mm to about 15 mm, or about 6 mm to about 10 mm. In various implementations, such dimension may particularly correspond to the outer diameter of the control body 102. In some implementations, the aerosol source member 104 may have a diameter of between about 4 mm and about 6 mm. In addition, the control body 102 and the aerosol source member may likewise be characterized in relation to overall length. For example, in some implementations the control body may have a length of about 40 mm to about 140 mm, about 45 mm to about 110 mm, or about 50 mm to about 100 mm. The aerosol source member may have a length of about 20 mm to about 60 mm, about 25 mm to about 55 mm, or about 30 mm to about 50 mm.

In the depicted implementation, the control body 102 includes a control component 123 that controls the various functions of the aerosol delivery device 100, including providing power to the electrical heating member 132. For example, the control component 123 may include a control circuit (which may be connected to further components, as further described herein) that is connected by electrically conductive wires (not shown) to the power source 124. In various implementations, the control circuit may control when and how the heating assembly 128, and particularly the heating member 132, receives electrical energy to heat the inhalable substance medium 110 for release of the inhalable substance for inhalation by a consumer. In some implementations, such control may be activated by a flow sensor and/or actuation of pressure sensitive switches or the like, which are described in greater detail hereinafter.

As described above, the aerosol delivery device 100 of example implementations may include circuitry in the context of either an electronic cigarette or a heat-not-burn device, or even in the case of a device that includes the functionality of both. FIG. 15 depicts circuit diagrams of the aerosol delivery device according to various example implementations of the present disclosure. As shown, the aerosol delivery device includes a flow sensor 120, control component 123, power source 124, indicator 126, and heating member 132. As described above, the control component is coupled to and configured to controllably power the heating member that is configured to convert electricity to heat and thereby vaporize components of aerosol precursor composition. As shown, the control component includes a buck regulator circuit 402 coupled to the heating member, and configured to step down voltage and step up current from the power source to the heating member to thereby power the heating member. The buck regulator circuit may or may not include a feedback feature. One example of a suitable buck regulator circuit includes the model ADP2165 or model ADP2166 DC-to-DC regulator from Analog Devices, which does include a feedback feature.

As shown in FIG. 15, in examples in which the buck regulator circuit 402 has a feedback feature, the control component 123 includes an operational amplifier circuit 404 coupled to the heating member 132 and buck regulator circuit. The operational amplifier circuit in these examples may be configured to amplify an output voltage from the heating member to produce a higher voltage that is fed back to the buck regulator circuit. In some examples such as those shown, the operational amplifier circuit is a non-inverting operational amplifier circuit. As also shown in FIG. 15, the buck regulator circuit 402 may include a power stage 406 configured to step down the voltage and step up the current from the power source 124, and a feedback control circuit 408 configured to use the higher voltage from the operational amplifier circuit 404 to regulate an output voltage from the buck regulator circuit to the heating member 132. The feedback control circuit may further include an error amplifier 410 and a pulse width modulation (PWM) comparator 412. The error amplifier may be configured to produce a control voltage based on a comparison of the higher voltage and a reference voltage. And the PWM comparator may be configured to use the control voltage to produce a PWM waveform that is used to regulate the output voltage from the buck regulator circuit to the heating member. In some examples, the aerosol delivery device 100 has terminals including a positive terminal 414 to which the power source 124 is connected or connectable. The control component 123 may further include a high-side load switch (LS) 416 between the buck regulator circuit 402 and the positive terminal, with the high--side load switch being configured to connect and disconnect the power source to and from a load including the heating member 132, and limit input current to the buck regulator circuit. This also acts as a protection circuit just in case the current spikes above a threshold safety factor. That is, the high-side load switch also acts as a safety feature in that it ensures that the input current doesn't go above the threshold safety factor. Even further, the flow sensor 120 may be between the positive terminal 414 and the high-side load switch 416. The sensor may be configured to produce a measurement of pressure caused by airflow through at least a portion of the aerosol delivery device 100, and convert the measurement of pressure to a corresponding electrical signal. A processor 418 of the control component 123 may be configured to receive the corresponding electrical signal and control the high-side load switch to connect the power source 124 to the load in response thereto. And in some examples, the aerosol delivery device 100 further includes a resistor R1 coupled in series between the operational amplifier circuit 404 and the buck regulator circuit 402. In these examples, the resistor may be configured to limit current fed back to the buck regulator circuit from the operational amplifier circuit. Other implementations of circuitry for the aerosol delivery device are described in U.S. patent application Ser. No. 15/916,696 to Sur, entitled: Buck Regulator With Operational Amplifier Feedback For An Aerosol Delivery Device, filed concurrently herewith, and which is incorporated herein by reference.

As noted, the control components may be configured to closely control the amount of heat provided to the inhalable substance medium 110. While the heat needed to volatilize the aerosol-forming substance in a sufficient volume to provide a desired dosing of the inhalable substance for a single puff can vary for each particular substance used, in some implementations the heating member may heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 220° C., at least 300° C., or at least 350° C. It can be particularly desirable, however, to avoid heating to temperatures substantially in excess of about 550° C. in order to avoid degradation and/or excessive, premature volatilization of the aerosol-forming substance. Heating specifically should be at a sufficiently low temperature and sufficiently short time so as to avoid significant combustion (preferably any combustion) of the inhalable substance medium. The present disclosure may particularly provide the components of the present device in combinations and modes of use that will yield the inhalable substance in desired amounts at relatively low temperatures. As such, yielding may refer to one or both of generation of the aerosol within the device and delivery out of the device to a consumer. In specific implementations, the heating temperature may be about 130° C. to about 310° C., about 140° C. to about 300° C., about 150° C. to about 290° C., about 170° C. to about 270° C., or about 180° C. to about 260° C. In other implementations, the heating temperature may be about 210° C. to about 390° C., about 220° C. to about 380° C., about 230° C. to about 370° C., about 250° C. to about 350° C., or about 280° C. to about 320° C.

The duration of heating may be controlled by a number of factors, as discussed in greater detail hereinbelow. Heating temperature and duration may depend upon the desired volume of aerosol and ambient air that is desired to be drawn through aerosol delivery device, as further described herein. The duration, however, may be varied depending upon the heating rate of the heating member, as the device may be configured such that the heating member is energized only until a desired temperature is reached. Alternatively, duration of heating may be coupled to the duration of a puff on the article by a consumer. Generally, the temperature and time of heating will be controlled by one or more components contained in the control housing, as noted above.

In various implementations, the electrical heating assembly may include any device suitable to provide heat sufficient to facilitate release of the inhalable substance for inhalation by a consumer. In certain implementations, the electrical heating assembly may include a resistance heating member. Useful heating members may be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time-based current control is employed. Useful heating members also are chemically non-reactive with the materials comprising the inhalable substance medium being heated so as not to adversely affect the flavor or content of the aerosol or vapor that is produced. Exemplary, non-limiting, materials that may comprise the heating member include carbon, graphite, carbon/graphite composites, metals, metallic and non-metallic carbides, nitrides, silicides, inter-metallic compounds, cermets, metal alloys, and metal foils. In particular, refractory materials may be useful. Various, different materials can be mixed to achieve the desired properties of resistivity, mass, thermal conductivity, and surface properties. In some implementations, refractory materials may be useful. Various, different materials may be mixed to achieve the desired properties of resistivity, mass, and thermal conductivity. In specific aspects, metals that are able to be utilized include, for example, nickel, chromium, alloys of nickel and chromium (e.g., nichrome), and steel. Materials that may be useful for providing resistance or resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

As seen in FIGS. 3 and 4, the heating assembly 128 of the depicted implementation comprises an outer cylinder 130 and a plurality of heater prongs 132 that extend from a receiving base 134. In some implementations, such as those wherein the inhalable substance medium comprises a tube structure, the heater prongs 132 may be configured to extend into a cavity defined by the inner surface of the inhalable substance medium. In other implementations, such as the depicted implementation wherein the inhalable substance medium comprises a solid or semi-solid structure, the plurality of heater prongs 132 are configured to penetrate into the inhalable substance medium 110 contained in the heated end 106 of the aerosol source member 104 when the aerosol source member 104 is inserted into the control body 102. In such implementations, one or more of the components of the heating assembly 128, including the heater prongs 132 and/or the receiving base 134, may be constructed of a non-stick or stick-resistant material, for example, certain aluminum, copper, stainless steel, carbon steel, and ceramic materials. In other implementations, one or more of the components of the heating assembly 128, including the heater prongs 132 and/or the receiving base 134, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™. In addition, although in the depicted implementation there are multiple heater prongs that are substantially equally distributed about the receiving base 134, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 136, including up to about 25%, up to about 50%, up to about 75%, and up to about the full length of the receiving chamber 136. In still other implementations, the heating assembly 128 may take on other configurations. Examples of other heater configurations that may be adapted for use in the present disclosure per the discussion provided above can be found in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., which are incorporated herein by reference in their entireties.

The amount of inhalable material released by the inventive device 100 may vary based upon the nature of the inhalable material. Preferably, the device 100 is configured with a sufficient amount of the inhalable material, with a sufficient amount of any aerosol-former, and to function at a sufficient temperature for a sufficient time to release a desired amount over a course of use. The amount may be provided in a single inhalation from the device 100 or may be divided so as to be provided through a number of puffs from the article over a relatively short length of time (e.g., less than 30 minutes, less than 20 minutes, less than 15 minutes, less than 10 minutes, or less than 5 minutes). Examples of nicotine levels and wet total particulate matter that may be delivered are described in U.S. Pat. No. 9,078,473 to Worm et al., which is incorporated herein by reference.

In various implementations, the control body 102 may include one or more openings or apertures 122 therein for allowing entrance of ambient air into the interior of the receiving chamber 136. In such a manner, in some implementations the receiving base 134 may also include apertures. Thus, in some implementations when a consumer draws on the mouth end of the aerosol source member 104, air can be drawn through the apertures of the control body 102 and the receiving base 134 into the receiving chamber 136, pass into the aerosol source member 104, and be drawn through the inhalable substance medium 110 of the aerosol source member 104 for inhalation by the consumer. In some implementations, the drawn air carries the inhalable substance through the optional filter 114 and out of an opening at the mouth end 108 of the aerosol source member 104. With the heating member 132 positioned inside the inhalable substance medium 110, the heating member 132 may be activated to heat the inhalable substance medium 110 and cause release of the inhalable substance through the aerosol source member 104.

In some implementations, it may be useful to provide some indication of when the aerosol source member 104 has achieved the proper distance of insertion into the receiving chamber 136 such that the heating member 132 is positioned in the inhalable substance medium 110. For example, the aerosol source member 104 may include one or more markings on the exterior thereof (e.g., on the outer surface of the aerosol source member 104). In other implementations, a single mark may indicate the depth of insertion required to achieve this position. Alternatively, proper insertion distance may be indicated by the aerosol source member 104 "bottoming out" against the base of the receiving chamber 136, such as, for example, against the receiving base 134, or any other such means that may enable a consumer to recognize and understand that the aerosol source member 104 has been inserted sufficiently in the receiving chamber 136 to position the heating member 132 in the proper location relative to the inhalable substance medium 110.

In some implementations, the aerosol delivery device 100 may include a pushbutton, which may be linked to the control component for manual control of the heating assembly. For example, in some implementations the consumer may use the pushbutton to energize the heating member 132. Similar functionality tied to the pushbutton may be achieved by other mechanical means or non-mechanical means (e.g., magnetic or electromagnetic). Thusly, activation of the heating member 132 may be controlled by a single pushbutton. Alternatively, multiple pushbuttons may be provided to control various actions separately. One or more pushbuttons present may be substantially flush with the casing of the control body 102.

Instead of (or in addition to) any pushbuttons, the inventive device 100 of the present disclosure may include components that energize the heating member 132 in response to the consumer's drawing on the article (i.e., puff-actuated heating). For example, the device may include a switch or flow sensor 120 in the control body 102 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch. An exemplary mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the heating member 132 sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and the receiving chamber 136 may be included in the control body 102 so that pressure changes during draw are readily identified by the switch. Other exemplary puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

When the consumer draws on the mouth end of the device 100, the current actuation means may permit unrestricted or uninterrupted flow of current through the resistance heating member 132 to generate heat rapidly. Because of the rapid heating, it can be useful to include current regulating components to (i) regulate current flow through the heating member to control heating of the resistance element and the temperature experienced thereby, and (ii) prevent overheating and degradation of the inhalable substance medium 110. In some implementations, the current regulating circuit may be time-based. Specifically, such a circuit may include a means for permitting uninterrupted current flow through the heating member for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating member within the desired temperature range. Further, regulation may comprise simply allowing uninterrupted current flow until the desired temperature is achieved then turning off the current flow completely. The heating member may be reactivated by the consumer initiating another puff on the article (or manually actuating the push-button, depending upon the specific switch implementation employed for activating the heater). Alternatively, the subsequent regulation can involve the modulation of current flow through the heating member to maintain the heating member within a desired temperature range. In some implementations, so as to release the desired dosing of the inhalable substance, the heating member may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One exemplary time-based current regulating circuit can include a transistor, a timer, a comparator, and a capacitor. Suitable transistors, timers, comparators, and capacitors are commercially available and will be apparent to the skilled artisan. Exemplary timers are those available from NEC Electronics as C-1555C and from General Electric Intersil, Inc. as ICM7555, as well as various other sizes and configurations of so-called "555 Timers". An exemplary comparator is available from National Semiconductor as LM311. Further description of such time-based current regulating circuits is provided in U.S. Pat. No. 4,947,874 to Brooks et al., which is incorporated herein by reference in its entirety.

In light of the foregoing, it can be seen that a variety of mechanisms can be employed to facilitate actuation/deactuation of current to the heating member. For example, the device may include a timer for regulating current flow in the article (such as during draw by a consumer). The device may further include a timer responsive switch that enables and disables current flow to the heating member. Current flow regulation also can comprise use of a capacitor and components for charging and discharging the capacitor at a defined rate (e.g., a rate that approximates a rate at which the heating member heats and cools). Current flow specifically may be regulated such that there is uninterrupted current flow through the heating member for an initial time period during draw, but the current flow may be turned off or cycled alternately off and on after the initial time period until draw is completed. Such cycling may be controlled by a timer, as discussed above, which can generate a preset switching cycle. In specific implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations further can include components for generating the threshold voltage at the threshold input and components for generating the threshold voltage at the first input upon passage of the initial time period.

As noted above, the power source 124 used to provide power to the various electrical components of the device 100 may take on various implementations. Preferably, the power source is able to deliver sufficient energy to rapidly heat the heating member in the manner described above and power the device through use with multiple aerosol source members 104 while still fitting conveniently in the device 100. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series. Other power sources, such as rechargeable lithium-manganese dioxide batteries, may also be used. Any of these batteries or combinations thereof may be used in the power source, but rechargeable batteries are preferred because of cost and disposal considerations associated with disposable batteries. In implementations where rechargeable batteries are used, the power source 124 may further include charging contacts for interaction with corresponding contacts in a conventional recharging unit (not shown) deriving power from a standard 120-volt AC wall outlet, or other sources such as an automobile electrical system or a separate portable power supply. In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—i.e., an electric double-layer capacitor (EDLC)—may be used separate from or in combination with a battery. When used alone, the supercapacitor may be recharged before each use of the device 100. Thus, the present disclosure also may include a charger component that can be attached to the device between uses to replenish the supercapacitor. Thin film batteries may be used in certain implementations of the present disclosure.

As noted above, in various implementations, the aerosol delivery device 100 may comprise one or more indicators 126. Although in the depicted implementation, the indicator 136 is shown at an end of the control body 102, in various implementations the indicator 136 may be located on another portion or other portions of the control body 102. In some implementations, the indicators may be lights (e.g., light emitting diodes) that may provide indication of multiple aspects of use of the device. For example, a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating.

This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In addition to the implementations described above, in some implementations the inhalable substance medium may be configured as a liquid capable of yielding an aerosol upon application of sufficient heat, having ingredients commonly referred to as "smoke juice," "e-liquid" and "e-juice". Exemplary formulations for an aerosol-generating liquid are described in U.S. Pat. App. Pub. No. 2013/0008457 to Zheng et al., the disclosure of which is incorporated herein by reference in its entirety. Another implementation of the present disclosure is depicted in FIGS. 5-8. In particular, FIGS. 5-8 illustrate an aerosol delivery device 200 according to an example implementation of the present disclosure. The aerosol delivery device 200 may include a control body 202 and an aerosol source member 204. In various implementations, the aerosol source member 204 and the control body 202 may be permanently or detachably aligned in a functioning relationship. In this regard, FIG. 5 illustrates the aerosol delivery device 200 in a coupled configuration, whereas FIG. 6 illustrates the aerosol delivery device 200 in a decoupled configuration. Various mechanisms may connect the aerosol source member 204 to the control body 202 to result in a threaded engagement, a press-fit engagement, an interference fit, a sliding fit, a magnetic engagement, or the like. FIG. 7 illustrates a front schematic view of an aerosol delivery device 200 according to an example implementation of the present disclosure, and FIG. 8 illustrates a sectional view through the aerosol delivery device 200.

In various implementations, the aerosol delivery device 200 according to the present disclosure may have a variety of overall shapes, including, but not limited to an overall shape that may be defined as being substantially rod-like or substantially tubular shaped or substantially cylindrically shaped. In the implementations of FIGS. 5-8, the device 200 has a substantially round cross-section; however, other cross-sectional shapes (e.g., oval, square, triangle, etc.) also are encompassed by the present disclosure. Such language that is descriptive of the physical shape of the article may also be applied to the individual components thereof, including the control body 202 and the aerosol source member 204. In other implementations, the control body may take another hand-held shape, such as a small box shape.

In specific implementations, one or both of the control body 202 and the aerosol source member 204 may be referred to as being disposable or as being reusable. For example, the control body 202 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 204 may comprise a single-use device. A similar single use component for use with a control body is disclosed in U.S. Pat. No. 8,910,639 to Chang et al., which is incorporated herein by reference in its entirety.

In the depicted implementation, the aerosol source member 204 comprises a heated end 206, which is configured to be inserted into the control body 202, and a mouth end 208, upon which a user draws to create the aerosol. At least a portion of the heated end 206 may include the inhalable substance medium 210. As discussed in more detail below, the inhalable substance medium 210 may comprise tobacco-containing beads, tobacco shreds, tobacco strips, a tobacco cast sheet, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid, semi-solid, or moldable (e.g., extrudable) substrate. Representative types of solid and semi-solid inhalable substance medium constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein.

In various implementations, the aerosol source member 204, or a portion thereof, may be wrapped in an overwrap material 212 (see FIG. 6), which may be formed of any material useful for providing additional structure and/or support for the aerosol source member 204. In various implementations, the mouth end 208 of the aerosol source member 204 may include a filter 214, which may be made of a cellulose acetate or polypropylene material. The filter 214 may increase the structural integrity of the mouth end of the aerosol source member, and/or provide filtering capacity, if desired, and/or provide resistance to draw. The overwrap material may comprise a material that resists transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material may incorporate inorganic components. In various implementations, the overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The overwrap may also include a material typically used in a filter element of a conventional cigarette, such as cellulose acetate. Further, an excess length of the overwrap at the mouth end 208 of the aerosol source member may function to simply separate the inhalable substance medium 210 from the mouth of a consumer or to provide space for positioning of a filter material, as described below, or to affect draw on the article or to affect flow characteristics of the vapor or aerosol leaving the device during draw. Further discussions relating to the configurations for overwrap materials that may be used with the present disclosure may be found in U.S. Pat. No. 9,078,473 to Worm et al., which is incorporated herein by reference in its entirety.

In various implementations other components may exist between the inhalable substance medium 210 and the mouth end 208 of the aerosol source member 204, wherein the mouth end 208 may include a filter 214. For example, in some implementations one or any combination of the following may be positioned between the inhalable substance medium 210 and the mouth end 208 of the aerosol source member 204: an air gap; phase change materials for cooling air; flavor releasing media; ion exchange fibers capable of selective chemical adsorption; aerogel particles as filter medium; and other suitable materials.

As will be discussed in more detail below, the present disclosure employs a conductive heat source to heat the inhalable substance medium. In various implementations, the conductive heat source may comprise a heating assembly that includes a heating member in direct contact with, or in proximity to, the aerosol source member and particularly, the inhalable substance medium of the aerosol source member. The heating assembly and/or the heating member may be located in the control body and/or the aerosol source member, as will be discussed in more detail below. In some instances, the inhalable substance medium may include a plurality of beads or particles imbedded in, or otherwise part of, the inhalable substance medium that may serve as, or facilitate the function of the heating assembly.

In some devices, the heating member may comprise a resistive heating element. Resistive heating elements may be configured to produce heat when an electrical current is directed therethrough. In various implementations, the heating member may be provided in a variety forms, such as in the form of a foil, a foam, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in proximity to the inhalable substance medium. Alternatively, the heating member may be positioned in contact with a solid or semi-solid inhalable substance medium. Such configurations may heat the inhalable substance medium to produce an aerosol. A variety of conductive substrates that may be usable with the present disclosure are described in U.S. Pat. App. Pub. No. 2013/0255702 to Griffith et al., the disclosure of which is incorporated herein by reference in its entirety.

FIG. 7 illustrates a front schematic view of an aerosol delivery device 200 according to an example implementation of the present disclosure, and FIG. 8 illustrates a sectional view through the aerosol delivery device 200 of FIG. 7. The control body 202 of the depicted implementation comprises a housing 218 that includes an opening 219 defined in an engaging end thereof. The control body 202 also includes a flow sensor 220 (e.g., a puff sensor or pressure switch), a control component 223 (e.g., processing circuitry, individually or as part of a microcontroller, a printed circuit board (PCB) that includes a microprocessor and/or microcontroller, etc.), a power source 224 (e.g., a battery, which may be rechargeable, and/or a rechargeable supercapacitor), and an end cap that includes an indicator 226 (e.g., a light emitting diode (LED)). In one implementation, the indicator 226 may comprise one or more light emitting diodes, quantum dot-based light emitting diodes or the like. The indicator 226 may be in communication with the control component 223 and be illuminated, for example, when a user draws on the aerosol source member 204, when coupled to the control body 202, as detected by the flow sensor 220. As will be discussed in more detail below, the aerosol delivery device 200 of this example implementation also includes a heating assembly 228 that includes an outer cylinder 230 and a two-part heating member 232, 233.

As noted above, various visual indicators of operation and/or tactile indicators of operation and/or sound indicators of operation similarly are encompassed by the present disclosure. In addition, Applicant makes reference to various possible power sources, flow sensors, representative current regulating components, other electrical components, and further components as described above with respect to FIGS. 1-4, which are also applicable to the present example implementation.

Referring back to FIGS. 7 and 8, the control body 202 of the depicted implementation includes a heating assembly 228 configured to heat the inhalable substance medium 210 of the aerosol source member 204. Although the heating assembly of various implementations of the present disclosure may take a variety of forms, in the particular implementation depicted in FIGS. 7 and 8, the heating assembly 228 comprises an outer cylinder 230 and a two-part heating member comprising a base heating member 232 and a substrate heating member 233 that includes a plurality of heater projections 235. In the depicted implementation, the outer cylinder 230 and the base heating member 232 are located in the control body 202, and the substrate heating member 233 is located in the aerosol source member 204, proximate the inhalable substance medium 210. In such a manner, the substrate heating member 233 of the aerosol source member 204 may be configured to be received by, and/or otherwise engage with, the base heating member 232. In particular, in the depicted implementation the base heating member 232 includes one or more locating features 237 that are configured to be received by, and/or otherwise engage with, corresponding locating features 239 of the substrate heating member 233. For example, in the depicted implementation the locating features 237 of the base heating member 232 comprise one or more rounded protrusions (i.e., a "male" connection component) that are configured to be fittingly received by one or more corresponding rounded receiving notches (i.e., a "female" connection component) of the substrate heating member 233. It should be noted that in other similar implementations, the relative configuration of such connection components may be reversed, for example, such that the male receiving components are part of the substrate heating member 233 and the female connection components are part of the base heating member 232.

To further aid in engaging the substrate heating member 233 with the base heating member 232, in some implementations one or both of the base heating member 232 or the substrate heating member 233 may be constructed of, or otherwise include, a ferromagnetic material. As such, the substrate heating member 233 and the base heating member 232 may be configured to be magnetically attracted to each other in order to further aid in engagement between the components. In such a manner, and in combination with the configuration of the rounded locating features 237, 239, the substrate heating member 233 and the base heating member 232 may snap together and/or otherwise be self-locating. In some implementations, the base heating member 232 may comprise an electromagnet powered by the power source 224 and may be configured to be electrically actuated between a magnetized state and a demagnetized state (and vice versa) via control by the control component 223. In such manner, a magnetic interlock may be created between the control body 202 and the aerosol source member 204. In such implementations, the control component 223 may be further configured to demagnetize the electromagnetic base heating member 232 so as to eject the aerosol source member 204 upon one or more conditions, such as, for example, when the control component 223 determines that the aerosol source member 204 has been used to its capacity and/or the inhalable substance medium 210 has been depleted.

In some implementations, the control body 202 may be configured to authenticate an aerosol source member 204. For example, in some implementations, a component of the aerosol source member 204 (for example, the substrate heating member 233) may include one or more electronic components (for example, an RFID tag), which may include an integrated circuit, a memory component, a sensor, or the like. In various implementations, the electronic component of the aerosol source member 204 may be adapted to communicate with the control component 223 and/or with an external device by wired or wireless means. An example of an aerosol delivery system containing an RFID tag is described in U.S. Pat. App. Pub. No. 2017/0020191 to Lamb et al., which is incorporated herein by reference in its entirety.

In the depicted implementation, the outer cylinder 230 comprises a double-walled vacuum tube constructed of stainless steel so as to maintain heat generated by the base heating member 232 and the substrate heating member 233 within the outer cylinder 230, and more particularly, maintain heat generated by base heating member 232 and the substrate heating member 233 within the inhalable substance medium 210. In various implementations, the base heating member 232 and/or the substrate heating member 233 may be constructed of the same material or different materials. For example, one or both of the base heating member 232 and the substrate heating member 233 may be constructed of one more conductive materials, including, but not limited to, copper, aluminum, platinum, gold, silver, iron, steel, brass, bronze, graphite, or any combination thereof. In some implementations, one or more of these materials may be embedded in or otherwise included with another material. For example, in some implementations one or both the base heating member 232 or the substrate heating member 233 may be constructed of a ceramic material that includes a conductive metal material embedded or otherwise included therein. As one of skill in the art would appreciate, various material choices may be made in light of sustainability considerations, such as implementations where one or both the aerosol source member or the control body are configured to be disposable.

As illustrated, the heating assembly 228 may extend proximate an engagement end of the housing 218, and may be configured to substantially surround a portion of the heated end 206 of the aerosol source member 204 that includes the inhalable substance medium 210. In such a manner, the heating assembly 228 may define a generally tubular configuration. As illustrated in FIGS. 7 and 8, the outer cylinder 230 creates a receiving chamber 236. In such a manner, the outer cylinder 230 may comprise a nonconductive insulating material and/or construction including, but not limited to, an insulating polymer (e.g., plastic or cellulose), glass, rubber, ceramic, porcelain, a double-walled vacuum structure, or any combinations thereof.

As noted above, in the illustrated implementation, the outer cylinder 230 may also serve to facilitate proper positioning of the aerosol source member 204 when the aerosol source member 204 is inserted into the housing 218. In various implementations, the outer cylinder 230 of the heating assembly 228 may engage an internal surface of the housing 218 to provide for alignment of the heating assembly 228 with respect to the housing 218. Thereby, as a result of the fixed coupling between the heating assembly 228, a longitudinal axis of the heating assembly 228 may extend substantially parallel to a longitudinal axis of the housing 218. In particular, the support cylinder 230 may extend from the opening 219 of the housing 218 to the base heating member 232 to create the receiving chamber 236. In the illustrated implementation, an inner diameter of the outer cylinder 230 may be slightly larger than or approximately equal to an outer diameter of a corresponding aerosol source member 204 (e.g., to create a sliding fit) such that the outer cylinder 230 is configured to guide the aerosol source member 204 into the proper position (e.g., lateral position) with respect to the control body 202.

In the illustrated implementation, the heater projections 235 of the substrate heating member 233 are located in the approximate radial center of at least a portion of the inhalable substance medium 210 of the heated end 206 of the aerosol source member 204. In such a manner, when used in conjunction with a solid or semi-solid inhalable substance medium 210, the heater projections 235 may be in direct contact with the inhalable substance medium 210. In other implementations, such as when used in conjunction with an extruded inhalable substance medium that defines a tube structure, the heater projection 235 may be located inside of a cavity defined by an inner surface of the extruded tube structure, and would not contact the inner surface of the extruded tube structure.

Referring back to FIGS. 7 and 8, during use, the consumer initiates heating of the heating assembly 228, and in particular, the base heating member 232. Due to the engagement of the base heating member 232 and the substrate heating member 233, by heat transfer this also initiates heating of the substrate heating member 233 that is adjacent the inhalable substance medium 210 (or a specific layer thereof). Heating of the inhalable substance medium 210 releases the inhalable substance within the aerosol source member 204 so as to yield the inhalable substance. When the consumer inhales on the mouth end 208 of the aerosol source member 204, air is drawn into the aerosol source member 204 through openings or apertures 222 in the control body 202. The combination of the drawn air and the released inhalable substance is inhaled by the consumer as the drawn materials exit the mouth end 208 of the aerosol source member 204. In some implementations, to initiate heating, the consumer may manually actuate a pushbutton or similar component that causes the heating member of the heating assembly to receive electrical energy from the battery or other energy source. The electrical energy may be supplied for a pre-determined length of time or may be manually controlled. In some implementations, flow of electrical energy does not substantially proceed in between puffs on the device (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 220. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 204 may be removed from the control body 202 and discarded. In some implementations, further sensing elements, such as capacitive sensing elements and other sensors, may be used as discussed in U.S. patent applicaiton Ser. No. 15/707,461 to Phillips et al., which is incorporated herein by reference in its entirety.

In various implementations, the aerosol source member 204 may be formed of any material suitable for forming and maintaining an appropriate conformation, such as a tubular shape, and for retaining therein an inhalable substance medium 210. In some implementations, the aerosol source member 204 may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating member, as further discussed herein. While in some implementations, a heat resistant polymer may be used, in other implementations, the aerosol source member 204 may be formed from paper, such as a paper that is substantially straw-shaped. As further discussed herein, the aerosol source member 204 may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the inhalable substance medium. In addition, Applicant makes reference to various possible dimensions, further components, and possible compositions of the aerosol source member, including the inhalable substance medium, as described above with respect to FIGS. 1-4.

Referring back to FIGS. 7 and 8, the heated end 206 of the aerosol source member 204 is sized and shaped for insertion into the control body 202. In various implementations, the receiving chamber 236 of the control body 202 may be characterized as being defined by a wall with an inner surface and an outer surface, the inner surface defining the interior volume of the receiving chamber 236. For example, in the depicted implementations, the outer cylinder 230 defines an inner surface defining the interior volume of the receiving chamber 236. Thus, the largest outer diameter (or other dimension depending upon the specific cross-sectional shape of the implementations) of the aerosol source member 204 may be sized to be less than the inner diameter (or other dimension) at the inner surface of the wall of the open end of the receiving chamber 236 in the control body 202. In some implementations, the difference in the respective diameters may be sufficiently small so that the aerosol source member fits snugly into the receiving chamber 236, and frictional forces prevent the aerosol source member 204 from being moved without an applied force. On the other hand, the difference may be sufficient to allow the aerosol source member 204 to slide into or out of the receiving chamber 236 without requiring undue force.

In some implementations, the overall size of the aerosol delivery device 200 may take on a size that is comparative to a cigarette or cigar shape. Thus, the device may have a diameter of about 5 mm to about 25 mm, about 5 mm to about 20 mm, about 6 mm to about 15 mm, or about 6 mm to about 10 mm. In various implementations, such dimension may particularly correspond to the outer diameter of the control body 202. In some implementations, the aerosol source member 204 may have a diameter of between about 4 mm and about 6 mm. In addition, the control body 202 and the aerosol source member may likewise be characterized in relation to overall length. For example, in some implementations the control body may have a length of about 40 mm to about 120 mm, about 45 mm to about 110 mm, or about 50 mm to about 100 mm. The aerosol source member may have a length of about 20 mm to about 60 mm, about 25 mm to about 55 mm, or about 30 mm to about 50 mm. In the depicted implementation, the control body 202 includes a control component 223 that controls the various functions of the aerosol delivery device 200, including providing power to the base heating member 232 and the substrate heating member 233. For example, the control component 223 may include a control circuit (which may be connected to further components, as further described herein) that is connected by electrically conductive wires (not shown) to the power source 224. Reference is made, for example, to the circuit diagrams of an aerosol delivery device shown in FIG. 15 and as described above. In various implementations, the control circuit may control when and how the heating assembly 228, and particularly the base heating member 232, receives electrical energy to heat the substrate heating member 233 and thus the inhalable substance medium 210 for release of the inhalable substance for inhalation by a consumer. In some implementations, such control may be activated by a flow sensor and/or actuation of pressure sensitive switches or the like, which are described in greater detail hereinafter.

As noted, the control components may be configured to closely control the amount of heat provided to the inhalable substance medium 210. While the heat needed to volatilize the aerosol-forming substance in a sufficient volume to provide a desired dosing of the inhalable substance for a single puff can vary for each particular substance used, in some implementations the heating member may heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 220° C., at least 300° C., or at least 350° C. It can be particularly desirable, however, to avoid heating to temperatures substantially in excess of about 550° C. in order to avoid degradation and/or excessive, premature volatilization of the aerosol-forming substance. Heating specifically should be at a sufficiently low temperature and sufficiently short time so as to avoid significant combustion (preferably any combustion) of the inhalable substance medium. The present disclosure may particularly provide the components of the present device in combinations and modes of use that will yield the inhalable substance in desired amounts at relatively low temperatures. As such, yielding may refer to one or both of generation of the aerosol within the device and delivery out of the device to a consumer. In specific implementations, the heating temperature may be about 130° C. to about 310° C., about 140° C. to about 300° C., about 150° C. to about 290° C., about 170° C. to about 270° C., or about 180° C. to about 260° C. In other implementations, the heating temperature may be about 210° C. to about 390° C., about 220° C. to about 380° C., about 230° C. to about 370° C., about 250° C. to about 350° C., or about 280° C. to about 320° C.

The duration of heating may be controlled by a number of factors, as discussed in greater detail hereinbelow. Heating temperature and duration may depend upon the desired volume of aerosol and ambient air that is desired to be drawn through aerosol delivery device, as further described herein. The duration, however, may be varied depending upon the heating rate of the heating member, as the device may be configured such that the heating member is energized only until a desired temperature is reached. Alternatively, duration of heating may be coupled to the duration of a puff on the article by a consumer. Generally, the temperature and time of heating will be controlled by one or more components contained in the control housing, as noted above. Applicant makes reference to various possible control components and related functions as described above with respect to FIGS. 1-4, which are also applicable to the present example implementation.

In various implementations, the electrical heating assembly may include any device suitable to provide heat sufficient to facilitate release of the inhalable substance for inhalation by a consumer. In certain implementations, the electrical heating assembly may include a resistance heating member. Useful heating members may be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time-based current control is employed. Useful heating members also are chemically non-reactive with the materials comprising the inhalable substance medium being heated so as not to adversely affect the flavor or content of the aerosol or vapor that is produced. Applicant makes further reference to various possible materials for the heating member as described above with respect to FIGS. 1-4, which are also applicable to the present example implementation.

As seen in FIGS. 7 and 8, the electrical heating assembly 228 of the depicted implementation comprises an outer cylinder 230 and a two-part heating member comprising the base heating member 232 of the control body 202 and the substrate heating member 233 of the aerosol source member 204, wherein the substrate heating member 233 includes the plurality of heater projections 235. In some implementations, such as those wherein the inhalable substance medium comprises a tube structure, the heater projections 235 may be configured to extend into a cavity defined by the inner surface of the inhalable substance medium. In other implementations, such as the depicted implementation wherein the inhalable substance medium comprises a solid or semi-solid structure, the plurality of heater projections 235 extend into the inhalable substance medium 210. Although in the depicted implementation there are multiple heater projections that are substantially equally distributed about an end surface of the substrate heating member 233, it should be noted that in other implementations, any number of heater projections may be used, including as few as one, with any other suitable spatial configuration. Furthermore, in various implementations the length of the heater projections may vary. For example, in the depicted implementation the heater projections extend a relatively small distance, while in other implementations the heater projections may extend any portion of the length of the inhalable substance medium 210, including up to about 25%, up to about 50%, up to about 75%, and up to about the full length of the inhalable substance medium 210. In addition, in various implementations the relative overall size of the substrate heating member 233 and the inhalable substance medium 210 may vary. For example, in some implementations the linear length of the substrate heating member 233 may be larger than, equal to, or less than the linear length of the inhalable substance medium 210. In some implementations, the substrate heating member length may be about 10 mm to about 14 mm, and in some implementations, about 12 mm. In some implementations, the inhalable substance medium length may be about 19 mm to about 23 mm, and in some implementations, about 21 mm. In other implementations, the substrate heating member 233 may have a different configuration that does not include any projections, such as for example, a substrate heating member having a cylindrical or tubular shape. Applicant makes further reference to various other possible heater configurations described above with respect to FIGS. 1-4, which are also applicable to the present example implementation.

The amount of inhalable material released by the inventive device 200 may vary based upon the nature of the inhalable material. Preferably, the device 200 is configured with a sufficient amount of the inhalable material, with a sufficient amount of any aerosol-former, and to function at a sufficient temperature for a sufficient time to release a desired amount over a course of use. The amount may be provided in a single inhalation from the device 200 or may be divided so as to be provided through a number of puffs from the article over a relatively short length of time (e.g., less than 30 minutes, less than 20 minutes, less than 15 minutes, less than 10 minutes, or less than 5 minutes). Examples of nicotine levels and wet total particulate matter that may be delivered are described in U.S. Pat. No. 9,078,473 to Worm et al., which is incorporated herein by reference.

In various implementations, the control body 202 may include one or more apertures 222 therein for allowing entrance of ambient air into the interior of the receiving chamber 236. In such a manner, the base heating member 232 and the substrate heating member 233 may also include openings or apertures. Thus, in some implementations when a consumer draws on the mouth end of the aerosol source member 204, air can be drawn into the control body 202, through the base heating member 232 and the substrate heating member 233, and through the inhalable substance medium 210 for inhalation by the consumer. In some implementations, the drawn air carries the inhalable substance through the optional filter 214 and out of an opening at the mouth end 208 of the aerosol source member 204. With the substrate heating member 233 positioned proximate or inside the inhalable substance medium 210, the heating members 232, 233 may be activated to heat the inhalable substance medium 210 and cause release of the inhalable substance through the aerosol source member 204.

In some implementations, such as, for example, some implementations where magnetic materials are not used, it may be useful to provide an indication of when the aerosol source member 204 has achieved the proper distance of insertion into the receiving chamber such that the base heating member 232 and the substrate heating member 233 is properly positioned with respect to each other. For example, the aerosol source member 204 may include one or more markings on the exterior thereof (e.g., on the outer surface of the aerosol source member 204). In other implementations, a single mark may indicate the depth of insertion required to achieve this position. Alternatively, proper insertion distance may be indicated by the aerosol source member "bottoming out" against the base of the receiving chamber, or any other such means that may enable a consumer to recognize and understand that the aerosol source member 204 has been inserted sufficiently in the receiving chamber 236 to position the heating members 232, 233 with respect to each other.

In some implementations, the aerosol delivery device 200 may include a pushbutton, which may be linked to the control component for manual control of the heating assembly. For example, in some implementations the consumer may use the pushbutton to energize the base heating member 232. Similar functionality tied to the pushbutton may be achieved by other mechanical means or non-mechanical means (e.g., magnetic or electromagnetic). Thusly, activation of the base heating member 232 may be controlled by a single pushbutton. Alternatively, multiple pushbuttons may be provided to control various actions separately. One or more pushbuttons present may be substantially flush with the casing of the control body 202.

Instead of (or in addition to) any pushbuttons, the inventive device 200 of the present disclosure may include components that energize the base heating member 232 in response to the consumer's drawing on the article (i.e., puff-actuated heating). For example, the device may include a switch or flow sensor 220 in the control body 202 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch. An exemplary mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the base heating member 232 sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Applicant makes further reference to various other possible puff actuated mechanisms, and other switches, sensors, and the like as described above with respect to FIGS. 1-4, which are also applicable to the present example implementation.

When the consumer draws on the mouth end of the device 200, the current actuation means may permit unrestricted or uninterrupted flow of current through the resistance base heating member 232 to generate heat rapidly. Because of the rapid heating, it can be useful to include current regulating components to (i) regulate current flow through the heating member to control heating of the resistance element and the temperature experienced thereby, and (ii) prevent overheating and degradation of the inhalable substance medium 210. In some implementations, the current regulating circuit particularly may be time-based. Applicant makes further reference to various possible current regulating circuits relating to the heating member, including time-based circuits, described above with respect to FIGS. 1-4, which are also applicable to the present example implementation.

As noted above, the power source 224 used to provide power to the various electrical components of the device 200 may take on various implementations. Preferably, the power source is able to deliver sufficient energy to rapidly heat the heating member in the manner described above and power the device through use with multiple aerosol source members 204 while still fitting conveniently in the device 200. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series. Other power sources, such as rechargeable lithium-manganese dioxide batteries, may also be used. Any of these batteries or combinations thereof may be used in the power source, but rechargeable batteries are preferred because of cost and disposal considerations associated with disposable batteries. In implementations where rechargeable batteries are used, the power source 224 may further include charging contacts for interaction with corresponding contacts in a conventional recharging unit (not shown) deriving power from a standard 120-volt AC wall outlet, or other sources such as an automobile electrical system or a separate portable power supply. In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—i.e., an electric double-layer capacitor (EDLC)—may be used separate from or in combination with a battery. When used alone, the supercapacitor may be recharged before each use of the device 200. Thus, the present disclosure also may include a charger component that can be attached to the device between uses to replenish the supercapacitor. Thin film batteries may be used in certain implementations of the present disclosure.

As noted above, in various implementations, the aerosol delivery device 200 may comprise one or more indicators 226. Although in the depicted implementation, the indicator 236 is shown located at an end of the control body 202, in various implementations the indicator 236 may be located on another portion or other portions of the control body 202. In some implementations, the indicators may be lights (e.g., light emitting diodes) that may provide indication of multiple aspects of use of the device. For example, a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In addition to the implementations described above, in some implementations the inhalable substance medium may be configured as a liquid capable of yielding an aerosol upon application of sufficient heat, having ingredients commonly referred to as "smoke juice," "e-liquid" and "e-juice". Exemplary formulations for an aerosol-generating liquid are described in U.S. Pat. App. Pub. No. 2013/0008457 to Zheng et al., the disclosure of which is incorporated herein by reference in its entirety.

Another implementation of the present disclosure is depicted in FIGS. 9-12. In particular, FIGS. 9-12 illustrate an aerosol delivery device 300 according to an example implementation of the present disclosure. The aerosol delivery device 300 may include a control body 302 and an aerosol source member 304. In various implementations, the aerosol source member 304 and the control body 302 may be permanently or detachably aligned in a functioning relationship. In this regard, FIG. 9 illustrates the aerosol delivery device 300 in a coupled configuration, whereas FIG. 10 illustrates the aerosol delivery device 300 in a decoupled configuration. Various mechanisms may connect the aerosol source member 304 to the control body 302 to result in a threaded engagement, a press-fit engagement, an interference fit, a sliding fit, a magnetic engagement, or the like. FIG. 11 illustrates a front schematic view of an aerosol delivery device 300 according to an example implementation of the present disclosure, and FIG. 12 illustrates a sectional view through the aerosol delivery device 300.

In various implementations, the aerosol delivery device 300 according to the present disclosure may have a variety of overall shapes, including, but not limited to an overall shape that may be defined as being substantially rod-like or substantially tubular shaped or substantially cylindrically shaped. In the implementations of FIGS. 9-12, the device 300 has a substantially round cross-section; however, other cross-sectional shapes (e.g., oval, square, triangle, etc.) also are encompassed by the present disclosure. Such language that is descriptive of the physical shape of the article may also be applied to the individual components thereof, including the control body 302 and the aerosol source member 304. In other implementations, the control body may take another hand-held shape, such as a small box shape.

In specific implementations, one or both of the control body 302 and the aerosol source member 304 may be referred to as being disposable or as being reusable. For example, the control body 302 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 304 may comprise a single-use device. A similar single use component for use with a control body is disclosed in U.S. Pat. No. 8,910,639 to Chang et al., which is incorporated herein by reference in its entirety.

In the depicted implementation, the aerosol source member 304 comprises a heated end 306, which is configured to be inserted into the control body 302, and a mouth end 308, upon which a user draws to create the aerosol. At least a portion of the heated end 306 may include the inhalable substance medium 310. As discussed in more detail below, the inhalable substance medium 310 may comprise tobacco-containing beads, tobacco shreds, tobacco strips, a tobacco cast sheet, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid, semi-solid, or moldable (e.g., extrudable) substrate. Representative types of solid and semi-solid inhalable substance medium constructions and formulations are disclosed in U.S. Pat. No. 8,424,538 to Thomas et al.; U.S. Pat. No. 8,464,726 to Sebastian et al.;

U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein.

In various implementations, the aerosol source member 304, or a portion thereof, may be wrapped in an overwrap material 312, which may be formed of any material useful for providing additional structure and/or support for the aerosol source member 304. In various implementations, the mouth end 308 of the aerosol source member 304 may include a filter 314, which may be made of a cellulose acetate or polypropylene material. The filter 314 may increase the structural integrity of the mouth end of the aerosol source member, and/or provide filtering capacity, if desired, and/or provide resistance to draw. The overwrap material may comprise a material that resists transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material may incorporate inorganic components. In various implementations, the overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The overwrap may also include a material typically used in a filter element of a conventional cigarette, such as cellulose acetate. Further, an excess length of the overwrap at the mouth end 308 of the aerosol source member may function to simply separate the inhalable substance medium 310 from the mouth of a consumer or to provide space for positioning of a filter material, as described below, or to affect draw on the article or to affect flow characteristics of the vapor or aerosol leaving the device during draw. Further discussions relating to the configurations for overwrap materials that may be used with the present disclosure may be found in U.S. Pat. No. 9,078,473 to Worm et al., which is incorporated herein by reference in its entirety.

In various implementations other components may exist between the inhalable substance medium 310 and the mouth end 308 of the aerosol source member 304, wherein the mouth end 308 may include a filter 314. For example, in some implementations one or any combination of the following may be positioned between the inhalable substance medium 310 and the mouth end 308 of the aerosol source member 304: an air gap; phase change materials for cooling air; flavor releasing media; ion exchange fibers capable of selective chemical adsorption; aerogel particles as filter medium; and other suitable materials.

As will be discussed in more detail below, the present disclosure employs a conductive heat source to heat the inhalable substance medium. In various implementations, the conductive heat source may comprise a heating assembly that includes a heating member in direct contact with, or in proximity to, the aerosol source member and particularly, the inhalable substance medium of the aerosol source member. The heating assembly and/or the heating member may be located in the control body and/or the aerosol source member, as will be discussed in more detail below. In some instances, the inhalable substance medium may include a plurality of beads or particles imbedded in, or otherwise part of, the inhalable substance medium that may serve as, or facilitate the function of the heating assembly.

In some devices, the heating member may comprise a resistive heating element. Resistive heating elements may be configured to produce heat when an electrical current is directed therethrough. In various implementations, the heating member may be provided in a variety forms, such as in the form of a foil, a foam, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in proximity to the inhalable substance medium. Alternatively, the heating member may be positioned in contact with a solid or semi-solid inhalable substance medium. Such configurations may heat the inhalable substance medium to produce an aerosol. A variety of conductive substrates that may be usable with the present disclosure are described in U.S. Pat. App. Pub. No. 2013/0255702 to Griffith et al., the disclosure of which is incorporated herein by reference in its entirety.

FIG. 11 illustrates a front schematic view of an aerosol delivery device 300 according to an example implementation of the present disclosure, and FIG. 12 illustrates a sectional view through the aerosol delivery device 300 of FIG. 11. The control body 302 of the depicted implementation comprises a housing 318 that includes an opening 319 defined in an engaging end thereof. The control body 302 also includes a flow sensor 320 (e.g., a puff sensor or pressure switch), a control component 323 (e.g., processing circuitry, individually or as part of a microcontroller, a printed circuit board (PCB) that includes a microprocessor and/or microcontroller, etc.), a power source 324 (e.g., a battery, which may be rechargeable, and/or a rechargeable supercapacitor), and an end cap that includes an indicator 326 (e.g., a light emitting diode (LED)). In one implementation, the indicator 326 may comprise one or more light emitting diodes, quantum dot-based light emitting diodes or the like. The indicator 326 may be in communication with the control component 323 and be illuminated, for example, when a user draws on the aerosol source member 304, when coupled to the control body 302, as detected by the flow sensor 320. As will be discussed in more detail below, the aerosol delivery device 300 of this example implementation also includes a heating assembly 328 that includes a heating cylinder 330 and a flexible heating member 332.

As noted above, various visual indicators of operation and/or tactile indicators of operation and/or sound indicators of operation similarly are encompassed by the present disclosure. In addition, Applicant makes reference to various possible power sources, flow sensors, representative current regulating components, other electrical components, and further components as described above with respect to FIGS. 1-4, which are also applicable to the present example implementation.

Referring back to FIGS. 11 and 12, the control body 302 of the depicted implementation includes a heating assembly 328 configured to heat the inhalable substance medium 310 of the aerosol source member 304. Although the heating assembly of various implementations of the present disclosure may take a variety of forms, in the particular implementation depicted in FIGS. 11 and 12, the heating assembly 328 comprises an outer cylinder 330 and a flexible heating member 332 that substantially surrounds at least a portion of the heating cylinder 330. In the depicted implementation, the heating cylinder 330 and the flexible heating member 332 are located in the control body 302. FIG. 13 illustrates a top view of the flexible heating member 332 of the example implementation of the present disclosure, shown in an unwrapped, flattened state. In the depicted implementation, the flexible heating member 332 comprises two independently controllable heater circuits 340, 342. In various implementations, the flexible heating member 332 may take a variety of other forms, including, for example, including as few as one heater circuit, or more than two heater circuits, in which any one, some, or all of the circuits may be independently controllable. Although various other types of flexible heaters may be used, in the depicted implementation, the flexible heating member 332 comprises an internal conductive layer that is surrounded by a cover layer on one side and a base layer on the opposite side. In some implementations, the cover and base layers may be constructed of a polymide material, and the internal conductive layer may be constructed of one or more flexible copper layers. In various implementations the copper layer(s) may be separated from the cover and base layers by one or more adhesive layers. Other conductive materials may be fabricated from one or more of the following: Nichrome, Cupronickel, Kanthal, Molybdenum disilicide, barium titanate, and lead titanate.

In the depicted implementation, the heating cylinder 330 comprises a tube configured to conduct heat therethrough from the inside surface of the flexible heating member 332 (i.e., proximate the base layer) to the aerosol source member 304, which as will be discussed in more detail below, when inserted into the control body 302 is proximate the inside surface of the heating cylinder 330. In various implementations, the heating cylinder 330 may comprise a conductive material including, but not limited to, copper, aluminum, platinum, gold, silver, iron, steel, brass, bronze, graphite, or any combination thereof. In the depicted implementation, the heating cylinder 330 is constructed of stainless steel. While in various implementations, the flexible heating member 332 may be affixed to the heating cylinder 330 such through the use of one or more adhesives, and/or other mechanical means, in the depicted implementation, the flexible heating member 332 is affixed to the heating cylinder 330 using a layer of heat-shrink wrap that wraps around an outside surface of the flexible heating member 332. In some implementations, the flexible heating member 332 and heating cylinder 330 may be surrounded by an insulation cylinder (not shown), which may, in some implementations, comprise a nonconductive insulating material and/or construction including, but not limited to, an insulating polymer (e.g., plastic or cellulose), glass, rubber, ceramic, porcelain, a double-walled vacuum structure, or any combinations thereof.

As illustrated, the heating assembly 328 may extend proximate an engagement end of the housing 318, and may be configured to substantially surround a portion of the heated end 306 of the aerosol source member 304 that includes the inhalable substance medium 310. In such a manner, the heating assembly 328 may define a generally tubular configuration. As illustrated in FIGS. 11 and 12, the heating cylinder 330 creates a receiving chamber 336. A receiving base 334 is disposed at the end of the receiving chamber 336 opposite the opening 319. As such, the heating cylinder 330 may also serve to facilitate proper positioning of the aerosol source member 304 when the aerosol source member 304 is inserted into the housing 318. In various implementations, the heating cylinder 330 of the heating assembly 328 may engage an internal surface of the housing 318 to provide for alignment of the heating assembly 328 with respect to the housing 318. Thereby, as a result of the fixed coupling between the heating assembly 328, a longitudinal axis of the heating assembly 328 may extend substantially parallel to a longitudinal axis of the housing 318. In particular, the heating cylinder 330 may extend from the opening 319 of the housing 318 to receiving base 334 to create the receiving chamber 336. In the illustrated implementation, an inner diameter of the heating cylinder 330 may be slightly larger than or approximately equal to an outer diameter of a corresponding aerosol source member 304 (e.g., to create a sliding fit) such that the heating cylinder 330 is configured to guide the aerosol source member 304 into the proper position (e.g., lateral position) with respect to the control body 302.

In various implementations, the control body 302 is configured such that when the aerosol source member 304 is inserted into the control body 302, the heating cylinder 330 is proximate at least a portion of the inhalable substance medium 310 of the heated end 306 of the aerosol source member 304. In the depicted implementation, the control body 302 is configured such that when the aerosol source member 304 is inserted into the control body 302, the heating cylinder 330 is in direct contact with an outer surface of the aerosol source member 304, and proximate the inhalable substance medium 310 at the heated end 306 of the aerosol source member 304. In various implementations, the control body 302 may be used in conjunction with a solid or semi-solid inhalable substance medium 310. In addition, in various implementations, the heating cylinder 330 may be used in conjunction with additional heating members, which, in some implementations, may include the receiving base 334.

Referring back to FIGS. 11 and 12, during use, the consumer initiates heating of the heating assembly 328, and in particular, the flexible heating member 332. Due to the spatial relationship of the flexible heating member 332 and the heating cylinder 330, by heat transfer this also initiates heating of the inhalable substance medium 310 (or a specific layer thereof). Heating of the inhalable substance medium 310 releases the inhalable substance within the aerosol source member 304 so as to yield the inhalable substance. When the consumer inhales on the mouth end 308 of the aerosol source member 304, air is drawn into the aerosol source member 304 through openings or apertures 322 in the control body 302. The combination of the drawn air and the released inhalable substance is inhaled by the consumer as the drawn materials exit the mouth end 308 of the aerosol source member 304. In some implementations, to initiate heating, the consumer may manually actuate a pushbutton or similar component that causes the heating member of the heating assembly to receive electrical energy from the battery or other energy source. The electrical energy may be supplied for a pre-determined length of time or may be manually controlled. In some implementations, flow of electrical energy does not substantially proceed in between puffs on the device (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 320. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference in its entirety.

In various implementations, the aerosol source member 304 may be formed of any material suitable for forming and maintaining an appropriate conformation, such as a tubular shape, and for retaining therein an inhalable substance medium 310. In some implementations, the aerosol source member 304 may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating member, as further discussed herein. While in some implementations, a heat resistant polymer may be used, in other implementations, the aerosol source member 304 may be formed from paper, such as a paper that is substantially straw-shaped. As further discussed herein, the aerosol source member 304 may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the inhalable substance medium. In addition, Applicant makes reference to various possible dimensions, further components, and possible compositions of the aerosol source member, including the inhalable substance medium, as described above with respect to FIGS. 1-4.

Referring back to FIGS. 11 and 12, the heated end 306 of the aerosol source member 304 is sized and shaped for insertion into the control body 302. In various implementations, the receiving chamber 336 of the control body 302 may be characterized as being defined by a wall with an inner surface and an outer surface, the inner surface defining the interior volume of the receiving chamber 336. For example, in the depicted implementations, the heating cylinder 330 defines an inner surface defining the interior volume of the receiving chamber 336. Thus, the largest outer diameter (or other dimension depending upon the specific cross-sectional shape of the implementations) of the aerosol source member 304 may be sized to be less than the inner diameter (or other dimension) at the inner surface of the wall of the open end of the receiving chamber 336 in the control body 302. In some implementations, the difference in the respective diameters may be sufficiently small so that the aerosol source member fits snugly into the receiving chamber 336, and frictional forces prevent the aerosol source member 204 from being moved without an applied force. On the other hand, the difference may be sufficient to allow the aerosol source member 304 to slide into or out of the receiving chamber 336 without requiring undue force. In some implementations, the overall size of the aerosol delivery device 300 may take on a size that is comparative to a cigarette or cigar shape. Thus, the device may have a diameter of about 5 mm to about 25 mm, about 5 mm to about 20 mm, about 6 mm to about 15 mm, or about 6 mm to about 10 mm. In various implementations, such dimension may particularly correspond to the outer diameter of the control body 302. In some implementations, the aerosol source member 304 may have a diameter of between about 4 mm and about 6 mm. In addition, the control body 302 and the aerosol source member may likewise be characterized in relation to overall length. For example, in some implementations the control body may have a length of about 40 mm to about 120 mm, about 45 mm to about 110 mm, or about 50 mm to about 100 mm. The aerosol source member may have a length of about 20 mm to about 60 mm, about 25 mm to about 55 mm, or about 30 mm to about 50 mm.

In the depicted implementation, the control body 302 includes a control component 323 that controls the various functions of the aerosol delivery device 300, including providing power to the flexible heating member 332. For example, the control component 323 may include a control circuit (which may be connected to further components, as further described herein) that is connected by electrically conductive wires (not shown) to the power source 324. Reference is made, for example, to the circuit diagrams of an aerosol delivery device shown in FIG. 15 and as described above. In various implementations, the control circuit may control when and how the heating assembly 328, and particularly the flexible heating member 332, receives electrical energy to heat the heating cylinder 330 and thus the inhalable substance medium 310 for release of the inhalable substance for inhalation by a consumer. In some implementations, such control may be activated by a flow sensor and/or actuation of pressure sensitive switches or the like, which are described in greater detail hereinafter.

As noted above, in the depicted implementation, the flexible heating member 332 comprises two independently controllable heating circuits 340, 342, and in other implementations, the flexible heating member 332 may comprise more than two independently controllable heating circuits. As such, in various implementations, the control component 323 may independently control each of the heating circuits such that each or some of the heating circuits may exhibit different heating characteristics as compared to the others. For example, in the depicted implementation, at certain times, or at all times, the control component 323 may control the first heater circuit 340 differently than the second heater circuit 342, such that, for example, the first heater circuit 340 has a different heating profile, and/or the timing or heating temperature thereof is different than that of the second heater circuit 342. In other implementations, however, the heating characteristics of the heating circuits may the same.

As noted, the control components may be configured to closely control the amount of heat provided to the inhalable substance medium 310. While the heat needed to volatilize the aerosol-forming substance in a sufficient volume to provide a desired dosing of the inhalable substance for a single puff can vary for each particular substance used, in some implementations one or more of the heating circuits of the heating member may heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 220° C., at least 300° C., or at least 350° C. It can be particularly desirable, however, to avoid heating to temperatures substantially in excess of about 550° C. in order to avoid degradation and/or excessive, premature volatilization of the aerosol-forming substance. Heating specifically should be at a sufficiently low temperature and sufficiently short time so as to avoid significant combustion (preferably any combustion) of the inhalable substance medium. The present disclosure may particularly provide the components of the present device in combinations and modes of use that will yield the inhalable substance in desired amounts at relatively low temperatures. As such, yielding may refer to one or both of generation of the aerosol within the device and delivery out of the device to a consumer. In specific implementations, the heating temperature may be about 130° C. to about 310° C., about 140° C. to about 300° C., about 150° C. to about 290° C., about 170° C. to about 270° C., or about 180° C. to about 260° C. In other implementations, the heating temperature may be about 210° C. to about 390° C., about 220° C. to about 380° C., about 230° C. to about 370° C., about 250° C. to about 350° C., or about 280° C. to about 320° C.

The duration of heating for one or more of the heating circuits may be controlled by a number of factors, as discussed in greater detail hereinbelow. Heating temperature and duration may depend upon the desired volume of aerosol and ambient air that is desired to be drawn through aerosol delivery device, as further described herein. The duration, however, may be varied depending upon the heating rate of the heating member circuits, as the device may be configured such that the heating member circuits are energized only until a desired temperature is reached. Alternatively, duration of heating may be coupled to the duration of a puff on the article by a consumer. Generally, the temperature and time of heating will be controlled by one or more components contained in the control housing, as noted above. Applicant makes reference to various possible control components and related functions as described above with respect to FIGS. 1-4, which are also applicable to the present example implementation.

In various implementations, the electrical heating assembly may include any device suitable to provide heat sufficient to facilitate release of the inhalable substance for inhalation by a consumer. In certain implementations, the electrical heating assembly may include a resistance heating member. Useful heating members may be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time-based current control is employed. Useful heating members also are chemically non-reactive with the materials comprising the inhalable substance medium being heated so as not to adversely affect the flavor or content of the aerosol or vapor that is produced. Applicant makes further reference to various possible materials for the heating member as described above with respect to FIGS. 1-4, which are also applicable to the present example implementation.

As seen in FIGS. 11-14, the electrical heating assembly 328 of the depicted implementation comprises a heating cylinder 330 and a flexible heating member 332 that includes two independently controlled heater circuits 340, 342. In various implementations, the flexible heating member 332 may extend any distance along the inhalable substance medium 310 portion of the aerosol source member 304. For example, in various implementations, the flexible heating member 332 may extend up to about 25%, up to about 50%, up to about 75%, or up to about the full length of the inhalable substance medium 310. In addition, in various implementations the relative overall size of the flexible heating member 332 may vary. Applicant makes further reference to various other possible heater configurations described above with respect to FIGS. 1-4, which are also applicable to the present example implementation.

The amount of inhalable material released by the inventive device 300 may vary based upon the nature of the inhalable material. Preferably, the device 300 is configured with a sufficient amount of the inhalable material, with a sufficient amount of any aerosol-former, and to function at a sufficient temperature for a sufficient time to release a desired amount over a course of use. The amount may be provided in a single inhalation from the device 300 or may be divided so as to be provided through a number of puffs from the article over a relatively short length of time (e.g., less than 30 minutes, less than 20 minutes, less than 15 minutes, less than 10 minutes, or less than 5 minutes). Examples of nicotine levels and wet total particulate matter that may be delivered are described in U.S. Pat. No. 9,078,473 to Worm et al., which is incorporated herein by reference.

In various implementations, the control body 302 may include one or more apertures 322 therein for allowing entrance of ambient air into the interior of the receiving chamber 336. In such a manner, the receiving base 334 may also include openings or apertures. Thus, in some implementations when a consumer draws on the mouth end of the aerosol source member 304, air can be drawn into the control body 302, through the base receiving member 334, and through the inhalable substance medium 310 for inhalation by the consumer. In some implementations, the drawn air carries the inhalable substance through the optional filter 314 and out of an opening at the mouth end 308 of the aerosol source member 304. With the flexible heating member 332 and heating cylinder 330 positioned proximate the inhalable substance medium 310, the flexible heating member 332 and heating cylinder 330 may be activated to heat the inhalable substance medium 310 and cause release of the inhalable substance through the aerosol source member 304.

In some implementations, it may be useful to provide an indication of when the aerosol source member 304 has achieved the proper distance of insertion into the receiving chamber 336 such that the flexible heating member 332 and heating cylinder 330 are positioned proximate the inhalable substance medium 310. For example, the aerosol source member 304 may include one or more markings on the exterior thereof (e.g., on the outer surface of the aerosol source member 304). In other implementations, a single mark may indicate the depth of insertion required to achieve this position. Alternatively, proper insertion distance may be indicated by the aerosol source member "bottoming out" against the base of the receiving chamber 336 (such as, for example, against the receiving base 334) or any other such means that may enable a consumer to recognize and understand that the aerosol source member 304 has been inserted sufficiently in the receiving chamber 336 to position the inhalable substance medium 310 in relation to the flexible heating member 332 and the heating cylinder 330.

In some implementations, the aerosol delivery device 300 may include a pushbutton, which may be linked to the control component for manual control of the heating assembly. For example, in some implementations the consumer may use the pushbutton to energize the flexible heating member 332. Similar functionality tied to the pushbutton may be achieved by other mechanical means or non-mechanical means (e.g., magnetic or electromagnetic). Thusly, activation of the flexible heating member 332 may be controlled by a single pushbutton. Alternatively, multiple pushbuttons may be provided to control various actions separately. One or more pushbuttons present may be substantially flush with the casing of the control body 302.

Instead of (or in addition to) any pushbuttons, the inventive device 300 of the present disclosure may include components that energize the flexible heating member 332 in response to the consumer's drawing on the article (i.e., puff-actuated heating). For example, the device may include a switch or flow sensor 320 in the control body 302 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch. An exemplary mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the flexible heating member 332 sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Applicant makes further reference to various other possible puff actuated mechanisms, and other switches, sensors, and the like as described above with respect to FIGS. 1-4, which are also applicable to the present example implementation.

When the consumer draws on the mouth end of the device 300, the current actuation means may permit unrestricted or uninterrupted flow of current through the resistance flexible heating member 332 to generate heat rapidly. Because of the rapid heating, it can be useful to include current regulating components to (i) regulate current flow through the heating member to control heating of the resistance element and the temperature experienced thereby, and (ii) prevent overheating and degradation of the inhalable substance medium 310. In some implementations, the current regulating circuit particularly may be time-based. Applicant makes further reference to various possible current regulating circuits relating to the heating member, including time-based circuits, described above with respect to FIGS. 1-4, which are also applicable to the present example implementation.

As noted above, the power source 324 used to provide power to the various electrical components of the device 300 may take on various implementations. Preferably, the power source is able to deliver sufficient energy to rapidly heat the heating member in the manner described above and power the device through use with multiple aerosol source members 304 while still fitting conveniently in the device 300. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series. Other power sources, such as rechargeable lithium-manganese dioxide batteries, may also be used. Any of these batteries or combinations thereof may be used in the power source, but rechargeable batteries are preferred because of cost and disposal considerations associated with disposable batteries. In implementations where rechargeable batteries are used, the power source 324 may further include charging contacts for interaction with corresponding contacts in a conventional recharging unit (not shown) deriving power from a standard 120-volt AC wall outlet, or other sources such as an automobile electrical system or a separate portable power supply. In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—i.e., an electric double-layer capacitor (EDLC)—may be used separate from or in combination with a battery. When used alone, the supercapacitor may be recharged before each use of the device 300. Thus, the present disclosure also may include a charger component that can be attached to the device between uses to replenish the supercapacitor. Thin film batteries may be used in certain embodiments of the present disclosure.

As noted above, in various implementations, the aerosol delivery device 300 may comprise one or more indicators 326. Although in the depicted implementation, the indicator 336 is shown located at an end of the control body 302, in various implementations the indicator 336 may be located on another portion or other portions of the control body 302. In some implementations, the indicators may be lights (e.g., light emitting diodes) that may provide indication of multiple aspects of use of the device. For example, a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In addition to the implementations described above, in some implementations the inhalable substance medium may be configured as a liquid capable of yielding an aerosol upon application of sufficient heat, having ingredients commonly referred to as "smoke juice," "e-liquid" and "e-juice". Exemplary formulations for an aerosol-generating liquid are described in U.S. Pat. Pub. No. 2013/0008457 to Zheng et al., the disclosure of which is incorporated herein by reference in its entirety.

The present disclosure provides devices and methods of using devices that use electrical energy to heat a heat source, which in turn heats a tobacco or tobacco derived material (preferably without combusting the tobacco or tobacco derived material to any significant degree) to form an inhalable substance such as an aerosol, the articles being sufficiently compact to be considered "hand-held" devices.

In certain implementations, the device may particularly be characterized as smoking articles. As used herein, the term is intended to mean a device or article that provides the taste and/or the sensation (e.g., hand-feel or mouth-feel) of smoking a cigarette, cigar, or pipe without the actual combustion of any component of the device. The term smoking device or article does not necessarily indicate that, in operation, the device produces smoke in the sense of the by-product of combustion or pyrolysis. Rather, smoking relates to the physical action of an individual in using the device—e.g., holding the device in a hand, drawing on one end of the device, and inhaling from the device. In further implementations, the inventive devices may be characterized as being vapor-producing devices, aerosolization devices, or pharmaceutical delivery devices. Thus, the devices may be arranged so as to provide one or more substances in an inhalable state.

It should be noted that although the aerosol source member and control body may be provided together as a complete smoking article or pharmaceutical delivery article generally, the components also may be provided separately. For example, the present disclosure also encompasses a disposable unit for use with a reusable smoking article or a reusable pharmaceutical delivery article. In specific implementations, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various implementations of an aerosol source member (or cartridge) are described in U.S. Pat. No. 9,078,473 to Worm et al., which is incorporated herein by reference.

In addition to the disposable unit, the present disclosure further may be characterized as providing a separate control body for use in a reusable smoking article or a reusable pharmaceutical delivery article. In specific implementations, the control body may generally be a housing having a receiving end (which may include a receiving chamber with an open end) for receiving a heated end of a separately provided aerosol source member. The control body may further include an electrical energy source that provides power to an electrical heating member, which may be a component of the control body or may be included in aerosol source member to be used with the control unit. For example, in some implementations, the electrical energy source may power a heating assembly that, in some implementations, may include one or more prongs that form the heating member, and the heating assembly may have associated electrical contacts that connect the heating member to the electrical energy source. In other implementations, the heating assembly may include a flexible heating member that substantially envelopes a heating cylinder. In other implementations, instead of including a unitary heating member, the heating assembly may comprise separate heating member components, with one component as part of the control body and another component as part of the aerosol source member. In various implementations, the control body may also include further components, including an electrical power source (such as a battery), components for actuating current flow into the heating member, and components for regulating such current flow to maintain a desired temperature for a desired time and/or to cycle current flow or stop current flow when a desired temperature has been reached or the heating member has been heating for a desired length of time. In some implementations, the control unit further may comprise one or more pushbuttons associated with one or both of the components for actuating current flow into the heating member, and the components for regulating such current flow. The control body may also include one or more indicators, such as lights indicating the heater is heating and/or indicating the number of puffs remaining for an aerosol source member that is used with the control body.

Although the various figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the present disclosure will come to mind to one skilled in the art to which this disclosure pertains having the benefit of the teachings presented in the foregoing descriptions and the associated drawings. Therefore, it is to be understood that the present disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

That which is claimed:

1. An aerosol delivery device configured to yield an inhalable substance, the aerosol delivery device comprising:
   a control body having a closed distal end and an open engaging end;
   a heating member;
   a control component located within the control body and configured to control the heating member;
   a power source located within the control body and configured to provide power to the control component; and
   a removable aerosol source member that includes an inhalable substance medium, the aerosol source member being configured to be inserted into the engaging end of the control body and defining a heated end and a mouth end, the heated end configured, when inserted into the control body, to be positioned proximate the heating member,
   wherein the heating member is configured to provide heat to at least a portion of the aerosol source member so as to form an inhalable aerosol, the aerosol configured to be drawn through the aerosol source member, wherein the heating member comprises a flexible heating member that surrounds a heating cylinder located within a portion of the engaging end of the control body, and wherein the control component is configured to provide an operating current that is at or between a range of approximately 2.5 Amps to approximately 10 Amps.

2. An aerosol delivery device configured to yield an inhalable substance, the aerosol delivery device comprising:
   a control body having a closed distal end and an open engaging end;
   a heating member;
   a control component located within the control body and configured to control the heating member;
   a power source located within the control body and configured to provide power to the control component; and
   a removable aerosol source member that includes an inhalable substance medium, the aerosol source member being configured to be inserted into the engaging end of the control body and defining a heated end and a mouth end, the heated end configured, when inserted into the control body, to be positioned proximate the heating member,
   wherein the heating member is configured to provide heat to at least a portion of the aerosol source member so as to form an inhalable aerosol, the aerosol configured to be drawn through the aerosol source member,
   wherein the heating member comprises a flexible heating member that surrounds a heating cylinder located within a portion of the engaging end of the control body, and
   wherein the control component is configured to provide up to approximately 96% efficiency of the power source.

3. An aerosol delivery device configured to yield an inhalable substance, the aerosol delivery device comprising:
   a control body having a closed distal end and an open engaging end;
   a heating member;
   a control component located within the control body and configured to control the heating member;
   a power source located within the control body and configured to provide power to the control component; and
   a removable aerosol source member that includes an inhalable substance medium, the aerosol source member being configured to be inserted into the engaging end of the control body and defining a heated end and a mouth end, the heated end configured, when inserted into the control body, to be positioned proximate the heating member,
   wherein the heating member is configured to provide heat to at least a portion of the aerosol source member so as to form an inhalable aerosol, the aerosol configured to be drawn through the aerosol source member,
   wherein the heating member comprises a flexible heating member that surrounds a heating cylinder located within a portion of the engaging end of the control body, and
   wherein the control component is configured to establish a time to reach temperature of less than approximately 10 seconds.

\* \* \* \* \*

UNITED STATES PATENT AND TRADEMARK OFFICE
CERTIFICATE OF CORRECTION

| | | |
|---|---|---|
| PATENT NO. | : 12,102,118 B2 | Page 1 of 1 |
| APPLICATION NO. | : 15/916834 | |
| DATED | : October 1, 2024 | |
| INVENTOR(S) | : Sur et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 582 days.

Signed and Sealed this
Second Day of September, 2025

Coke Morgan Stewart
*Acting Director of the United States Patent and Trademark Office*